(12) United States Patent
Williams et al.

(10) Patent No.: US 6,548,569 B1
(45) Date of Patent: *Apr. 15, 2003

(54) MEDICAL DEVICES AND APPLICATIONS OF POLYHYDROXYALKANOATE POLYMERS

(75) Inventors: Simon F. Williams, Sherborn, MA (US); David P. Martin, Arlington, MA (US); Frank A. Skraly, Somerville, MA (US)

(73) Assignee: Metabolix, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/535,146

(22) Filed: Mar. 24, 2000

Related U.S. Application Data

(60) Provisional application No. 60/142,238, filed on Jul. 2, 1999, and provisional application No. 60/126,180, filed on Mar. 25, 1999.

(51) Int. Cl.⁷ .................. C08L 67/04; C08G 63/91; C08G 65/329
(52) U.S. Cl. .................. 523/124; 521/17; 521/27; 521/539; 525/411; 525/450
(58) Field of Search .................. 523/124; 525/411, 525/450; 521/17, 27, 539

(56) References Cited

U.S. PATENT DOCUMENTS

| | | |
|---|---|---|
| 4,792,336 A | 12/1988 | Hlavacek et al. |
| 4,826,493 A | 5/1989 | Martini et al. |
| 4,910,145 A | 3/1990 | Holmes et al. |
| 5,085,629 A | 2/1992 | Goldberg et al. |
| 5,124,371 A * | 6/1992 | Tokiwa et al. ............ 523/124 |
| 5,250,430 A | 10/1993 | Peoples et al. |
| 5,271,961 A | 12/1993 | Mathiowitz et al. |
| 5,306,286 A | 4/1994 | Stack et al. |
| 5,334,698 A | 8/1994 | Witholt et al. |
| 5,443,458 A | 8/1995 | Eury |
| 5,480,394 A | 1/1996 | Ishikawa |
| 5,480,794 A | 1/1996 | Peoples et al. |
| 5,489,470 A | 2/1996 | Noda |
| 5,502,116 A | 3/1996 | Noda |
| 5,502,158 A * | 3/1996 | Sinclair et al. ............ 523/124 |
| 5,512,669 A | 4/1996 | Peoples et al. |
| 5,534,432 A | 7/1996 | Peoples et al. |
| 5,536,564 A | 7/1996 | Noda |
| 5,551,954 A | 9/1996 | Buscemi et al. |
| 5,563,239 A | 10/1996 | Hubbs et al. |
| 5,625,030 A * | 4/1997 | Williams et al. ............ 524/450 |
| 5,629,077 A | 5/1997 | Turnlund et al. |
| 5,646,217 A * | 7/1997 | Hammond ............ 525/450 |
| 5,670,161 A | 9/1997 | Healy et al. |
| 5,705,187 A | 1/1998 | Unger |
| 5,711,933 A | 1/1998 | Bichon et al. |
| 5,814,071 A | 9/1998 | McDevitt et al. |
| 5,824,751 A * | 10/1998 | Hori et al. ............ 523/124 |
| 5,834,582 A * | 11/1998 | Sinclair et al. ............ 523/124 |
| 5,855,619 A | 1/1999 | Caplan et al. |
| 5,876,452 A | 3/1999 | Athanasiou et al. |
| 5,876,455 A | 3/1999 | Harwin |
| 5,935,506 A | 8/1999 | Schmitz et al. |
| 5,994,478 A * | 11/1999 | Asrar et al. ............ 525/450 |
| 6,245,537 B1 * | 6/2001 | Williams et al. ............ 435/135 |

FOREIGN PATENT DOCUMENTS

| | | | |
|---|---|---|---|
| EP | 0 349 505 A2 | 3/1990 | |
| EP | 0 452 111 | * 10/1991 | |
| EP | 507554 | * 10/1992 | ............ 523/124 |
| EP | 0 628 586 A1 | 6/1994 | |
| EP | 0 754 467 A1 | 1/1997 | |
| GB | 2166354 A | 5/1986 | |
| WO | WO 95/03356 A1 | 2/1995 | |
| WO | WO 95/23250 A1 | 8/1995 | |
| WO | WO 95/33874 A1 | 12/1995 | |
| WO | WO 96/08535 A1 | 3/1996 | |
| WO | WO 97/07153 A1 | 2/1997 | |
| WO | WO 98/39453 A1 | 9/1998 | |
| WO | WO 98/48028 A1 | 10/1998 | |
| WO | WO 98/51812 A2 | 11/1998 | |
| WO | WO 99/32536 A1 | 7/1999 | |

OTHER PUBLICATIONS

Ex parte Simpson 61 USPQ 2d 1009 BPAI, Oct. 31, 2001.*
Principles of Polymerization, Third Edition, George Dolion Wiles and Sons p. 24, 1981.*
Polymer Science Dictionary, Second Edition Mark Alger, Chapman and Hall, pp. 32–33, 1989.*
Fraser, et al., "Controlled release of a GnRH agonist from a polyhydroxybutyric acid implant–reversible suppression of the menstrual cycle in the macaque," *Acta Endocrinol* 121:841–848 (1989).
Holmes, et al., "Applications of PHB–13 a microbially produced biodegradable thermoplastic," *Phys Technol* 16:32–36 (1985).

(List continued on next page.)

Primary Examiner—Peter Szekely
(74) Attorney, Agent, or Firm—Holland & Knight LLP

(57) ABSTRACT

Devices formed of or including biocompatible polyhydroxyalkanoates are provided with controlled degradation rates, preferably less than one year under physiological conditions. Preferred devices include sutures, suture fasteners, meniscus repair devices, rivets, tacks, staples, screws (including interference screws), bone plates and bone plating systems, surgical mesh, repair patches, slings, cardiovascular patches, orthopedic pins (including bone filling augmentation material), adhesion barriers, stents, guided tissue repair/regeneration devices, articular cartilage repair devices, nerve guides, tendon repair devices, atrial septal defect repair devices, pericardial patches, bulking and filling agents, vein valves, bone marrow scaffolds, meniscus regeneration devices, ligament and tendon grafts, ocular cell implants, spinal fusion cages, skin substitutes, dural substitutes, bone graft substitutes, bone dowels, wound dressings, and hemostats. The polyhydroxyalkanoates can contain additives, be formed of mixtures of monomers or include pendant groups or modifications in their backbones, or can be chemically modified, all to alter the degradation rates. The polyhydroxyalkanoate compositions also provide favorable mechanical properties, biocompatibility, and degradation times within desirable time frames under physiological conditions.

20 Claims, 3 Drawing Sheets

OTHER PUBLICATIONS

Korsatko, et al., "The of the molecular weight of poly–D(-)–3–hydroxybutyric acid on its use as a retard matrix for sustained drug release," *8th Europ. Congress of Biopharmaceutics and Pharmokinetics* 1:234–242 (1987).

Modelli, et al., "Kinetics of aerobic polymer degradation in soil by means of the ASTM D 5988–96 standard method," *J. Environ Polym Degr* 7:109–116 (1999).

Renstad, et al., "The influence of processing induced differences in molecular structure on the biological and non–biological degradation of poly (3–hydroxybutyrate–co–3–hydroxyvalerate), P(3–HB–co–3–HV)," *Polymer Degradation and Stability* 63:201–211 (1999).

Agostini, et al., "Synthesis and Characterization of Poly–β–Hydroxybutyrate. I. Synthesis of Crystalline DL Poly–β–Hydroxybutyrate from DL–β–Butyrolactone," *Polym. Sci.*, Part A–1 9:2775–87 (1981).

Bailey, et al., "Synthesis of Poly—caprolactone via a free radical mechanism. Free radical ring–opening polymerization of 2–methylene–1,3–dioxepane," *J. Polym. Sci. Polym. Chem.* 20:3021–30 (1992).

Behrend, "PHB as a bioresorbable material for intravascular stents," *American J. Cardiol.* p. 45, TCT Abstracts (Oct. 1998).

Breuer, et al., "Tissue Engineering Lamb Heart Valve Leaflets," *Biotechnology & Bioengineering* 50:562–67 (1996).

Bruhn & Mëller, "Preparation and characterization of spray–dried Poly(DL–Lactide) Micro Spheres," *Proceed. Intern. Symp. Control. Rel. Bioact. Mater.* 18:668–69 (1991).

Byrom, "Miscellaneous Biomaterials," in *Biomaterials* (D. Byrom, ed.), pp. 333–359 MacMillan Publishers: London, 1991.

Campbell & Bailey, "Mechanical properties of suture materials in vitro and after in vivo implantation in horses," *Vet. Surg.* 21(5):355–61 (1992).

Chu, et al., *Wound Closure Biomaterials and Devices* CRC Press–Boca Raton, 1996.

Conti, et al., "Use of polylactic acid for the preparation of microparticulate drug delivery systems," *J. Microencapsulation* 9:153–166 (1992).

Damien & Parsons, "Bone graft and bone graft substitutes: a review of current technology and applications," *J. Appl. Biomater.* 2(3):187–208 (1991).

De Groot, "Meniscal tissue regeneration in porous 50/50 copoly(L–lactide/epsilon–caprolactone) implants," *Biomaterials* 18(8):613–22 (1997).

Domb, et al., *Handbook of Biodegradable Polymers* (Harwood Academic Publishers:Amsterdam, The Netherlands, 1997).

Dubois, et al., "Macromolecular Engineering of Polylactones and Polylactides. 12. Study of the Depolymerization Reactions of Poly (ε–caprolactone) with Functional Aluminum Alkoxide End Groups," *Macromolecules* 26:4407–12 (1993).

Duvernoy, et al., "A biodegradable patch used as a pericardial substitute after open heart operations," *Ann. Thorac. Surg.* 48(6):803–12 (1989).

Gerngross & Martin, "Enzyme–catalyzed synthesis of poly [(R)–(-)–3–hydroxybutyrate]: formation of macroscopic granules in vitro," *Proc. Natl. Acad. Sci. USA* 92:6279–83 (1995).

Gross, et al., "Polymerization of β–Monosubstituted–β–propiolactones Using Trialkylaluminum–Water Catalytic Systems and Polymer Characterization," *Macromolecules* 21:2657–68 (1988).

Gugala, et al., "Regeneration of segmental diaphyseal defects in sheep tibiae using resorbable polymeric membranes: a preliminary study," *J. Orthop. Trauma.* 13(3):187–95 (1999).

Hadlock, et al., "Ocular cell monolayers cultured on biodegradable substrates," *Tissue Eng.* 5(3):187–96 (1999).

Hein, et al., "Biosynthesis of poly(4–hydroxybutyric acid) by recombinant strains of *Escherichia coli*," *FEMS Microbiol. Lett.* 153:411–18 (1997).

Heydorn, et al., "A new look at pericardial substitutes," *J. Thorac. Cardiovasc. Surg.* 94:291–96 (1987).

Hocking & Marchessault, "Syndiotactic poly[(R, S)–β–hydroxybutyrate] isolated from methylaluminoxane–catalyzed polymerization," *Polym. Bull.* 30:163–70 (1993).

Hocking & Marchessault, "Biopolymers" in *Chemistry and Technology of Biodegradable Polymers*, (G.J.L. Griffin, ed.), pp. 48–98, Chapman and Hall: London, 1994.

Holmes, et al., "Biologically Produced (R)–3–hydroxyalkanoate Polymers and Copolymers," in *Developments in Crystalline Polymers* (Bassett, ed.), pp. 1–65, Elsevier: London, 1988.

Hori, et al., "Chemical synthesis of high molecular weight poly(3–hydroxybutyrate–co–4–hydroxybutyrate)," *Polymer* 36:4703–05 (1996).

Hori, et al., "Ring–Opening Copolymerization of Optically Active β–Butyrolactone with Several Lactones Catalyzed by Distannoxane Complexes: Synthesis of New Biodegradable Polyesters," *Macromolecules* 26:4388–90 (1993).

Hori, et al., "Ring–Operating Polymerization of Optically Active β–Butyrolactone Using Distannoxane Catalysts: Synthesis of High Molecular Wright Poly(3–hydroxybutyrate)," *Macromolecules* 26:5533–34 (1993).

Hutmacher, et al., "A review of material properties of biodegradable and bioresorbable polymers and devices for GTR and GBR applications," *Int. J. Oral Maxillofac. Implants* 11(5):667–78 (1996).

Kemnitzer, et al., "Preparation of predominantly Syndietactic Poly(β–hydroxybutyrate) by the Tributylin Mathoxide Catalyzed Ring–Opening Polymerization of racemic β–Butyrolactone," *Macromolecules* 26:1221–29 (1993).

Kishida, et al., "Formulation–assisted biodegradable polymer matrices," *Chemical and Pharmaceutical Bulletin* 37:1954–56 (1989).

Koosha, "Preparation and characterization of biodegradable polymeric drug carriers," Ph.D. Dissertation, 1989, Univ. Nottingham, UK., *Diss. Abstr. Int. B* 51:1206 (1990).

Koosha, et al., "Polyhydroxybutyrate as a drug carrier," *Crit. Rev. Ther. Drug Carrier Syst.* 6(2):117–30 (1989).

Kusaka et al., "Microbial synthesis and Physical Properties of ultra–high–molecular–weight poly ([(R)–3–hydroxybutyrate]," *Pure Appl. Chem.* A35:319–35 (1998).

Lafferty, et al., "Microbial Production of Poly–b–hydroxybutyric acid" in *Biotechnology* (Rehm & Reed, Ed.), pp. 135–76, Verlagsgesellschaft:Weinheim, 1988.

Lamba, et al., *Polyurethanes in Biomedical Applications* (CRC Press:Boca Raton, Florida, 1998).

Lanza, et al., *Principles of Tissue Engineering* (Academic Press:Austin, 1997).

Le Borgne, et al., "Stereoselective polymerization of β–butyrolactone," *Polymer.* 30:2312–19 (1989).

Malm, et al., "Enlargement of the right ventricular outflow tract and the pulmonary artery with a new biodegradable patch in transannular position," *Eur. Surg. Res.* 26(5):298–308 (1994).

Malm, et al., "Prevention of postoperative pericardial adhesions by closure of the pericardium with absorbable polymer patches. An experimental study," *J. Thorac. Cardiovasc. Surg.* 104(3):600–07 (1992).

Mathiowitz & Langer, "Polyanhydride microspheres as drug delivery systems" in *Microcapsules Nanopart. Med. Pharm.* (Donbrow, ed.), pp. 99–123 (CRC:Boca Raton, Florida, 1992).

Maysinger, et al., "Microencapsulation and the Grafting of Genetically Transformed Cells as Therapeutic Strategies to rescue Degenerating Neurons of the CNS," *Reviews in the Neurosciences,* 6:15–33 (1995).

McMillin, et al., "Elastomers for Biomedical Applications," *Rubber Chemistry and Technology* 67:417–46 (1994).

Müller, et al., "Poly(hydroxyalkanoates): A Fifth Class of Physiologically Important Organic Biopolymers," *Angew. Chem. Int. Ed. Engl.* 32:477–502 (1993).

Nakamura, et al., "Microbial synthesis and characterization of poly–(3–hydroxybutyrate–co–4–hydroxybutyrate)," *Macromol.* 25:4237–41 (1992).

Niklason, et al., "Functional arteries grown in vitro," *Science* 284(5413):489–93 (1999).

Nobes, et al., "Polyhydroxyalkanoates: Materials for delivery systems," *Drug Del.* 5:167–77 (1998).

Ogawa, et al., "A New Technique to Efficiently Entrap Leuprolide Acetate into Microcapsules of Poly Lactic Acid or Copoly(Lactic/Glycolic) Acid," *Chem. Pharm. Bull.* 36:1095–103 (1988).

Otera, et al., "Distannoxane as reverse micelle–type catalyst: novel solvent effect on reaction rate of transesterification," *J. Org. Chem.* 54:4013–14 (1989).

Otera, et al., "Distannoxane–catalysed transesterification of 1,n–Dioldiacetates, Selective transformation of either of chemically equivalent functional groups," *J. Chem. Soc. Commun.* 1742–43 (1991).

Otera, et al., "Novel distannoxane–catalyzed transesterification and a new entry to, –unsaturated carboxylic acid," *Tetrahedron Lett.,* 27:2383–86 (1986).

Otera, et al., "Novel template effects of distannoxane catalysts in highly efficient transesterification and esterification," *J. Org. Chem .* 56:5307–11 (1991).

Rivard, et al., "Fibroblast seeding and culture in biodegradable porous substrates," *J. Appl. Biomater.* 6(1):65–68 (1995).

Saito, et al., "Microbial synthesis and properties of poly(3–hydroxybutyrate–co–4–hydroxybutyrate) in *Comamonas acidovorans,*" *Int. J. Biol. Macromol.* 16(2):99–104 (1994).

Shinoka, et al., "Creation of viable pulmonary artery autografts through tissue engineering," *J. Thorac. Cardiovasc. Surg.* 115(3):536–46 (1998).

Shinoka, et al., "Tissue engineering heart valves: valve leaflet replacement study in a lamb model" *Ann. Thorac. Surg.* 60(6 Suppl):S513–6 (1995).

Shinoka & Mayer, "New frontiers in tissue engineering: tissue engineered heart valves" in *Synthetic Bioabsorbable Polymer Scaffolds* (Atala & Mooney, eds.), pp. 187–198 Birkhäuser Boston, 1997.

Sim, et al., "PHA synthase controls the molecular weight and polydispersity of polyhydroxybutyrate in vivo," *Nat. Biotechnol.* 15(1):63–67 (1997).

Speer & Warren, "Arthroscopic shoulder stabilization. A role for biodegradable materials," *Clin. Orthop.* (291):67–74 (1993).

Steinbüchel & Valentin, "Diversity of bacterial polyhydroxyalkanoic acids," *FEMS Microbiol. Lett.* 128:219–28 (1995).

Steinbüchel & Wiese, "A Pseudomonas strain accumulating polyesters of 3–hydroxybutyric acid and medium–chain–length 3–hydroxyalkanoic acids," *Appl. Microbiol. Biotechno l.* 37:691–97 (1992).

Steinbüchel, "Polyhydroxyalkanoic Acids," in *Biomaterials* (D. Byrom ed.), pp. 123–213, MacMillan Publishers: London, 1991.

Talja, et al., "Bioabsorbable and biodegradable stents in urology," *J. Endourol.* 11(6):391–97 (1997).

Tanahashi, et al., "Thermal Properties and Stereoregularity of Poly(3–hydroxybutyrate) Prepared from optically Active β–Butyrolactone with a Zinc–Based Catalyst," *Macromolecules* 24:5732–33 (1991).

Tanguay, et al., "Current status of biodegradable stents," *Cardiol. Clin.* 12(4):699–713 (1994).

Tsuruta, et al., *Biomedical Applications of Polymeric Materials* (CRC Press, Boca Raton, Florida, 1993).

Unverdorben, et al., "Polyhydroxybutyrate (PHB) Biodegradable Stent–Experience in the Rabbit," *American J. Cardiol.* p. 46, TCT Abstracts (Oct. 1998).

Valentin, et al., "Production of poly(3–hydroxybutyrate–co–4–hydroxybutyrate) in recombinant *Escherichia coli* grown on glucose," *J. Biotechnol.* 58:33–38 (1997).

Von Schroeder, et al., "The use of polylactic acid matrix and periosteal grafts for the reconstruction of rabbit knee articular defects," *J. Biomed. Mater. Res.* 25(3):329–39 (1991).

Wallen & Rohwedder, "Poly–β–hydroxyalakaonate from Activated Sludge," *Environ. Sci. Technol.* 8:576–79 (1974).

Widmer & Mikos, "Fabrication of biodegradable polymer scaffolds for tissue engineering" in *Frontiers in Tissue Engineering* (Patrick, et al., Eds.) Ch. II.5, pp. 107–120 (Elsevier Science, New York, 1998).

Williams & Peoples, "Making plastics green," *Chem. Br.* 33:29–32 (1997).

Williams & Peoples, "Biodegradable plastics from plants," *Chemtech* 26:38–44 (1996).

Xie, et al., "Ring–opening Polymerization of β–Butyrolactone by Thermophilic Lipases," *Macromolecules* 30:6997–98 (1997).

Yamada, et al., "Development of a dural substitute from synthetic bioabsorbable polymers," *J. Neurosurg.* 86(6):1012–17 (1997).

Zund, et al., "The in vitro constuction of a tissue engineered bioprosthetic heart valve," *Eur. J. Cardiothorac. Surg.* 11(3):493–97 (1997).

\* cited by examiner

MEDICAL DEVICES AND APPLICATIONS OF POLYHYDROXYALKANOATE POLYMERS

CROSS-REFERENCE TO RELATED APPLICATIONS

Priority is claimed to U.S. Ser. No. 60/142,238, filed Jul. 2, 1999, and U.S. Ser. No. 60/126,180, filed Mar. 25, 1999.

FIELD OF THE INVENTION

The present invention generally relates to polyhydroxyalkanoate ("PHA") biopolymers and medical uses and application of these materials.

BACKGROUND OF THE INVENTION

In the medical area, a number of degradable polymers have been developed that break down in vivo into their respective monomers within weeks or a few months. Despite the availability of these synthetic degradable polymers, there is still a need to develop degradable polymers which can further extend the range of available properties, particularly mechanical properties.

Polyhydroxyalkanoates are natural, thermoplastic polyesters and can be processed by traditional polymer techniques for use in an enormous variety of applications, including consumer packaging, disposable diaper linings and garbage bags, food and medical products. Initial efforts focused on molding applications, in particular for consumer packaging items such as bottles, cosmetic containers, pens, and golf tees. U.S. Pat. Nos. 4,826,493 and 4,880,592 describe the manufacture of poly-(R)-3-hydroxybutyrate ("PHB") and poly-(R)-3-hydroxybutyrate-co-(R)-3-hydroxyvalerate ("PHBV") films and their use as diaper backsheet. U.S. Pat. No. 5,292,860 describes the manufacture of the PHA copolymer poly(3-hydroxybutyrate-co-3-hydroxyhexanoate) and the use of these polymers for making diaper backsheet film and other disposable items. Diaper back sheet materials and other materials for manufacturing biodegradable or compostable personal hygiene articles from PHB copolymers other than PHBV are described in PCT WO 95/20614, WO 95/20621, WO 95/23250, WO 95/20615, WO 95/33 874, WO 96/08535, and U.S. Pat. Nos. 5,502,116; 5,536,564; and 5,489,470.

One of the most useful properties of PHAs which readily distinguishes them from petrochemically-derived polymers is their biodegradability. Produced naturally by soil bacteria, PHAs are degraded upon subsequent exposure to these same bacteria in either soil, compost, or marine sediment. Biodegradation of PHAs is dependent upon a number of factors, such as the microbial activity of the environment and the surface area of the item. Temperature, pH, molecular weight, and crystallinity also are important factors. Biodegradation starts when microorganisms begin growing on the surface of the plastic and secrete enzymes which break down the polymer into hydroxy acid monomeric units, which are then taken up by the microorganisms and used as carbon sources for growth. In aerobic environments, the polymers are degraded to carbon dioxide and water, while in anaerobic environments the degradation products are carbon dioxide and methane (Williams & Peoples, CHEMTECH, 26:38–44 (1996)). While the mechanism for degradation of PHAs in the environment is widely considered to be via enzymatic attack and can be relatively rapid, the mechanism of degradation in vivo is generally understood to involve simple hydrolytic attack on the polymers' ester linkages, which may or may not be protein mediated. Unlike polymers comprising 2-hydroxyacids such as polyglycolic acid and polylactic acid, polyhydroxyalkanoates normally are comprised of 3-hydroxyacids and, in certain cases, 4-, 5-, and 6-hydroxyacids. Ester linkages derived from these hydroxyacids are generally less susceptible to hydrolysis than ester linkages derived from 2-hydroxyacids.

Researchers have developed processes for the production of a great variety of PHAs, and around 100 different monomers have been incorporated into polymers under controlled fermentation conditions (Steinbüchel & Valentin, FEMS Microbiol. Lett., 128:219–28 (1995)). There are currently only two commercially available PHA compositions: PHB and PHBV. Because of their great compositional diversity, PHAs with a range of physical properties can be produced (Williams & Peoples, CHEMTECH, 26:38–44 (1996)). The commercially available PHAs, PHB and PHBV, represent only a small component of the property sets available in the PHAs. For example, the extension to break of PHB and PHBV range from around 4 to 42%, whereas the same property for poly-4-hydroxybutyrate ("P4HB") is about 1000% (Saito & Doi, Int. J. Biol. Macromol. 16: 99–104 (1994)). Similarly, the values of Young's modulus and tensile strength for PHB and PHBV are 3.5 to 0.5 GPa and 40 to 16 MPa, respectively (for increasing HV content to 25 mol %), compared to 149 MPa and 104 MPa, respectively for P4HB (Saito & Doi, Int. J. Biol. Macromol. 16: 99–104 (1994)).

PHB and PHBV have been extensively studied for use in biomedical applications, in addition to their commercial use as a biodegradable replacement for synthetic commodity resins. These studies range from potential uses in controlled release (see, e.g., Koosha, et al., Crit. Rev. Ther. Drug Carrier Syst. 6:117–30 (1989) and Pouton & Akhtar, Adv. Drug Delivery Rev., 18:133–62 (1996)), to use in formulation of tablets, surgical sutures, wound dressings, lubricating powders, blood vessels, tissue scaffolds, surgical implants to join tubular body parts, bone fracture fixation plates, and other orthopedic uses, as described in PCT WO 98/51812. Wound dressings made from PHB are disclosed in GB 2166354 A to Webb, et al. One advanced medical development is the use of PHB and PHBV for preparing a porous, bioresorbable flexible sheet for tissue separation and stimulation of tissue regeneration in injured soft tissue described in EP 754467 A1 to Bowald et al. and EP 349505 A2. Reports have also described the use of PHBV to sustain cell growth (Rivard, et al., J. Appl. Biomat., 6:65–68 (1995)).

Besides biocompatibility, it is often desired that an implanted medical device should degrade after its primary function has been met. PHB and PHBV, the only PHAs tested as medical implants to date, have shown very long in vivo degradation periods, of greater than one year for PHB (Duvernoy, et al. Thorac. Cardiovasc. Surgeon 43:271–74 (1995); Malm, et al., J. Thorac. Cardiovasc. Surg. 104:600–07 (1992)). For many applications, this very long degradation time is undesirable as the persistence of polymer at a wound healing site may lead to a chronic inflammatory response in the patient. Slowly degrading PHB patches used to regenerate arterial tissue have been found to elicit a long term (greater than two years) macrophage response (Malm, et al., Eur. Surg. Res. 26:298–308 (1994)). Macrophages were identified as being involved in the degradation of the PHB implants and this long term macrophage response appears to indicate the presence of persistent, slowly degrading particulate material originating from the implant. Although a PHB patch used for repair of the pericardium was not seen by ordinary light microscopy after 12 months implantation, small residual particulate material was observed by polarized light microscopy (Malm, et al., *Scand J. Thor. Cardiovasc. Surg.* 26:9–14 (1992)). It is unclear whether this particulate material remains localized at the implant site or migrates throughout the body, possibly causing unforeseen complications. The biological fate, or medical impact of this particulate material, cannot be predicted without long term study. In order to minimize potential problems associated with slowly degrading PHAs, it is advantageous to utilize resorbable materials with faster in vivo degradation rates.

There has been only one report describing the biocompatibility or in vivo degradation of any other PHA polymer in biomedical applications (PCT WO 98/51812). U.S. Pat. No. 5,334,698 to Witholt et al. discloses medical articles manufactured with an optically active polyester isolated from *Pseudomonas oleovorans* cells; however, no examples or discussion of fabrication or biocompatibility testing are shown, and no methods are provided to obtain the polymer in a suitably pure form for in vivo medical use. Since bacteria suitable for production of these polymers may also produce an endotoxin, as well as other inflammatory mediators, it is important that the polymer be processed to remove these contaminants.

For many applications, the rate of PHA biodegradation is well suited to the required product lifetime. However, in certain cases it would be desirable to be able to exert more control over the rate at which the polymers breakdown in the environment. Such control would extend the range of applications for this class of polymers. For example, a PHA film may have suitable mechanical properties to be used as a mulch film, yet not have the most optimum rate of degradation for the application. The ability to be able to control the rate of degradation of the polymer in the environment would thus be a distinct advantage.

U.S. Pat. No. 5,935,506 discloses a PHB stent. The stent construct, which is reported to bioresorb rapidly, contains a large amount of plasticizer. However, the plasticized PHB approach fails to work, as greater than 90% stent stenosis was shown at four weeks (see Behrend, *American J. Cardiol.* p. 45, TCT Abstracts (October 1998); Unverdorben, et al., *American J. Cardiol.* p. 46, TCT Abstracts (October 1998)). It would be advantageous to provide a bioresorbable stent with improved mechanical properties and no plasticizer.

Thus while the polyhydroxyalkanoates offer a wide range of mechanical properties which are potentially useful in medical applications, their use particularly in vivo as resorbable polymers has been limited by their slow hydrolysis. It would thus be desirable to develop methods for controlling the rates of degradation of polyhydroxyalkanoates.

PCT WO 98/51812 discloses methods for making a wide range of biodegradable biocompatible polyester materials known as polyhydroxyalkanoates. These materials are made in high purity, and are suitable for use in in vivo medical applications.

It is therefore an object of this invention to provide new devices and uses for compositions comprising or derived from polyhydroxyalkanoates which degrade more readily in the environment and/or in vivo.

It is another object of this invention to provide methods for fabricating the articles and devices from these compositions.

SUMMARY OF THE INVENTION

Biocompatible polyhydroxyalkanoate compositions with controlled degradation rates have been developed. The compositions preferably include a biocompatible polyhydroxyalkanoate that has a controlled degradation rate of less than two years, more preferably less than one year, under physiological conditions. The degradation rates of the polymers can be manipulated through addition of various components to the polymeric composition, as well as selection of the chemical composition, molecular weight, processing conditions, and form of the final polymeric product. The chemical composition can be altered through selection of monomers which are incorporated into the polymer, by alteration of the linkages, chemical backbone or pendant groups, and/or by manipulation of the molecular weight. The polyhydroxyalkanoate composition can contain additives to alter the degradation rates. Porosity can be increased, hydrophilic substances included, and/or surface area exposed to water increased, all of which will increase the rate of degradation. Hydrophobic coatings or incorporation into or blending with hydrophobic substances with the polymers will decrease the rate of degradation.

Preferred devices include sutures, suture fasteners, meniscus repair devices, rivets, tacks, staples, screws (including interference screws), bone plates and bone plating systems, surgical mesh, repair patches, slings, cardiovascular patches, orthopedic pins (including bone filling augmentation material), heart valves and vascular grafts, adhesion barriers, stents, guided tissue repair/regeneration devices, articular cartilage repair devices, nerve guides, tendon repair devices, atrial septal defect repair devices, pericardial patches, bulking and filling agents, vein valves, bone marrow scaffolds, meniscus regeneration devices, ligament and tendon grafts, ocular cell implants, spinal fusion cages, skin substitutes, dural substitutes, bone graft substitutes, bone dowels, wound dressings, and hemostats. The polyhydroxyalkanoate composition can be used in both new and existing medical applications, including drug delivery and controlled release of drugs and other bioactive materials. These polyhydroxyalkanoate compositions can also be used to make or form coatings on a wide variety of devices, including stents, catheters, and sensors. Their advantages in new and existing applications can be the use of a biodegradable substitute material in the application, or the addition of some other desirable characteristic or attribute associated with the application or use, such as a mechanical or surface property, physical or chemical property, sterilization technique, biocompatibility, degradation mechanism, packaging preference, and/or a stability issue.

As demonstrated by the examples, these polyhydroxyalkanoate compositions, such as poly(4HB), have extremely favorable mechanical properties, as well as are biocompatible and degrade within desirable time frames under physiological conditions. These polyhydroxyalkanoate materials provide a wider range of polyhydroxyalkanoate degradation rates than are currently available.

Methods for processing these materials, particularly for therapeutic, prophylactic or diagnostic applications, or into devices which can be implanted or injected, are also described.

DETAILED DESCRIPTION OF THE INVENTION

Figure 1:
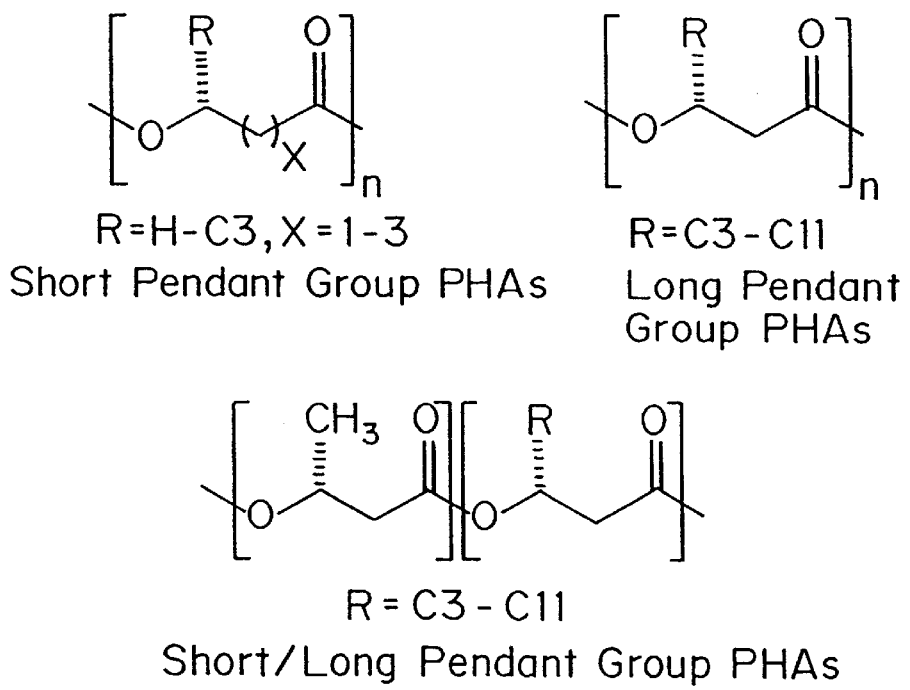
FIG. 1 is a schematic of PHA biopolymers broadly divided into groups according to the length of their pendant groups and their respective biosynthetic pathways.

Medical devices comprising biocompatible polyhydroxyalkanoate composition with controlled degradation rates have been developed.

I. Definitions

A "bioerodible polymer" is a water-insoluble polymer that is converted under physiological conditions into water soluble materials without regard to the specific mechanism involved in the erosion process. "Bioerosion" includes both physical processes (such as dissolution) and chemical processes (such as backbone cleavage which includes chain scission). The prefix "bio" indicates that the erosion occurs under physiological conditions, as opposed to other erosion processes, caused for example, by high temperature, strong acids or bases, UV light or weather conditions. The terms "bioresorption" and "bioabsorption" are used interchangeably and often imply that the polymer or its degradation products are removed by cellular activity (e.g., phagocytosis) in a biological environment.

As used herein in reference to polymers, the term "degrade" refer to cleavage of the polymer chain, such that the molecular weight stays approximately constant at the oligomer level and particles of polymer remain following degradation. The term "completely degrade" refers to cleavage of the polymer at the molecular level such that there is essentially complete mass loss. The term "degrade" as used herein includes "completely degrade" unless otherwise indicated.

In the preferred embodiment described herein, the polymer erodes under physiological conditions in less than two years, more preferably in less than one year.

Biocompatible refers to materials that do not elicit a toxic or severe immunological response following implantation or ingestion.

II. The Polyhydroxyalkanoate ("PHA") Compositions (1) Polymer Compositions

As used herein, "PHA materials" contain one or more units, for example between 10 and 100,000, and preferably between 100 and 30,000 units of the following formula I:

—OCR$^1$R$^2$(CR$^3$R$^4$)$_n$CO—;

wherein n is an integer, for example between 1 and 15, and in a preferred embodiment, between 1 and 4; and wherein R$^1$, R$^2$, R$^3$, and R$^4$ independently can be hydrocarbon radicals including long chain hydrocarbon radicals; halo- and hydroxy-substituted radicals; hydroxy radicals; halogen radicals; nitrogen-substituted radicals; oxygen-substituted radicals; and/or hydrogen atoms.

As used herein, the formula —(CR$^3$R$^4$)$_n$— is defined as including the following formulas:

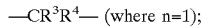
—CR$^3$R$^4$— (where n=1);

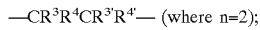
—CR$^3$R$^4$CR$^{3'}$R$^{4'}$— (where n=2);

and

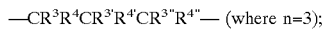
—CR$^3$R$^4$CR$^{3'}$R$^{4'}$CR$^{3''}$R$^{4''}$— (where n=3);

wherein R$^3$, R$^4$, R$^{3'}$, R$^{4'}$, R$^{3''}$, and R$^{4''}$ can be independently hydrocarbon radicals including long chain hydrocarbon radicals; halo- and hydroxy-substituted radicals; hydroxy radicals; halogen radicals; nitrogen-substituted radicals; oxygen-substituted radicals; and/or hydrogen atoms. Thus, formula I includes units derived from 3-hydroxyacids (n=1), 4-hydroxyacids (n=2), and 5-hydroxyacids (n=3).

These units may be the same in a homopolymer, or be more different units, as for example in a copolymer or terpolymer. The polymers typically have a molecular weight over 300, for example between 300 and 10$^7$, and in a preferred embodiment 10,000 to 10,000,000 Daltons.

The PHA materials may contain or be modified to include other molecules, such as bioactive and detectable compounds, surface active agents, other degradable or non-degradable polymers, as well as materials used to modify the mechanical properties of PHAs such as plasticizers, fillers, nucleating agents, colorants, stabilizers, modifiers and binders.

Representative PHAs which can be modified or formulated as described herein are described in Steinbüchel & Valentin, *FEMS Microbiol. Lett.*, 128:219–28 (1995).

PHB and P4HB possess very different physical properties. A range of PHA copolymers containing 4-hydroxybutyrate are either known or can be prepared with a range of intermediate properties between those of PHB and P4HB (Saito & Doi, *Int. J. Biol. Macromol.* 16:99–104 (1994)). However, biomedical applications, biocompatibility testing, and in vivo degradation of P4HB and its copolymers have not been reported. PHA copolymers of 4HB and 3HB varying in composition from 0 to 100% 4HB have been produced in *Alcaligenes eutrophus* (Nakamura, et al. *Macromol.* 25:4237–31(1992)) and from 64 to 100% 4HB in *Comamonas acidovorans* (Saito & Doi, *Int. J. Biol. Macromol.* 16:99–104 (1994)). However, these polymers were of modest molecular mass (133 10$^5$ to 5×10$^5$ g/mol, by GPC) compared to the molecular mass produced in recombinant *E. coli* (greater than 5×10$^5$ g/mol, GPC).

The PHA biopolymers may be broadly divided into three groups according to the length of their pendant groups and their respective biosynthetic pathways (FIG. 1). Those with short pendant groups, such as polyhydroxybutyrate (PHB), a homopolymer of R-3-hydroxybutyric acid (R-3HB) units, are highly crystalline thermoplastic materials, and have been known the longest (Lemoigne & Roukhelman, *Annales des fermentations* 5:527–36 (1925)). A second group of PHAs containing the short R-3HB units randomly polymerized with much longer pendant group hydroxy acid units were first reported in the early seventies (Wallen & Rohwedder, *Environ. Sci. Technol.*, 8:576–79 (1974)). A number of microorganisms which specifically produce copolymers of R-3HB with these longer pendant group hydroxy acid units are also known and belong to this second group (Steinbüchel & Wiese, *Appl. Microbiol. Biotechnol*, 37:691–97 (1992)). In the early eighties, a research group in The Netherlands identified a third group of PHAs, which contained predominantly longer pendant group hydroxy acids (De Smet, et al., *J. Bacteriol*, 154:870–78 (1983)).

Figure 2A:
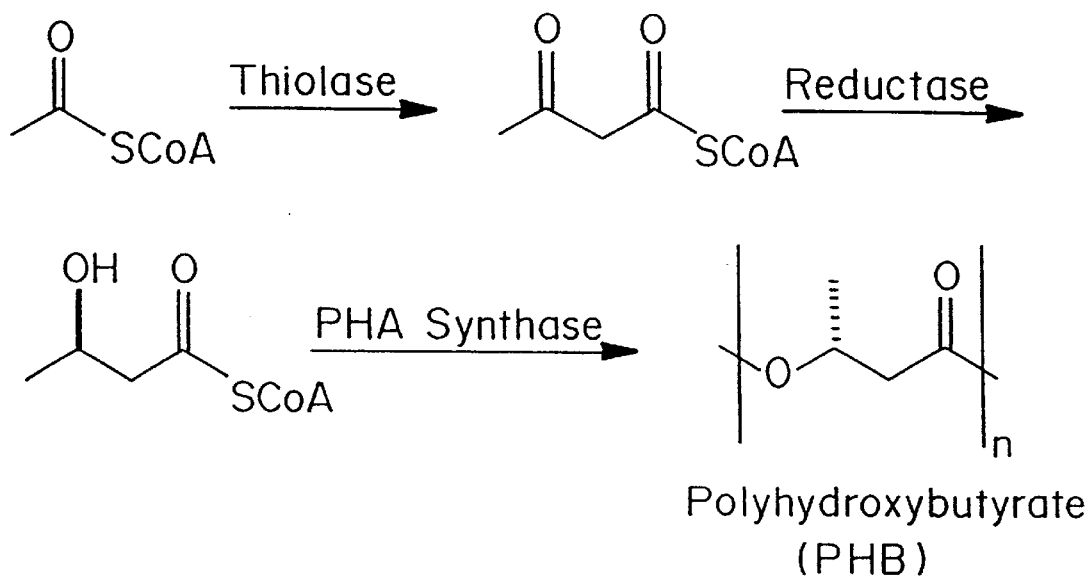
FIG. 2*a* is a schematic of the pathways by which short pendant group PHAs are derived.
Figure 2B:
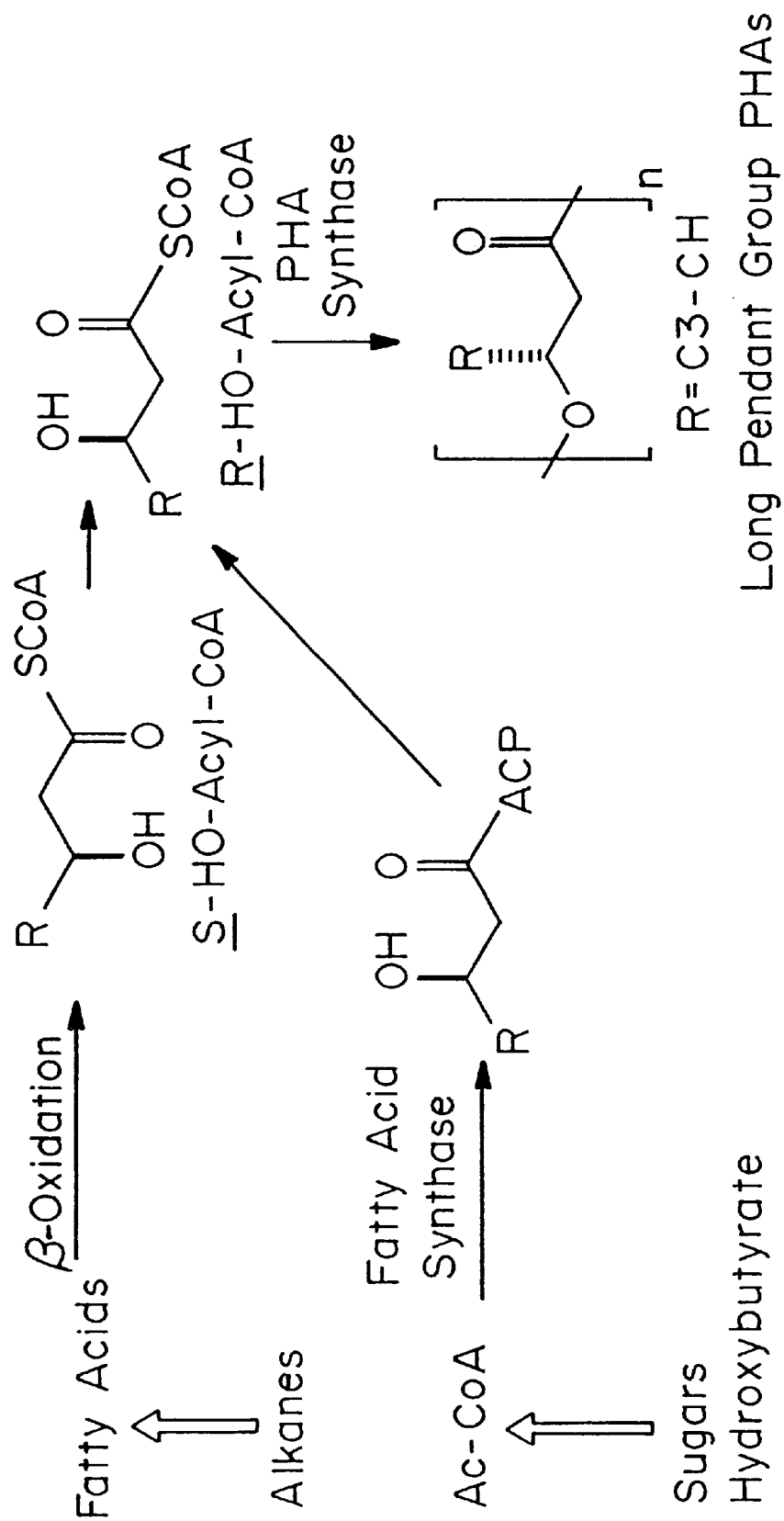
FIG. 2*b* is a schematic of the pathways by which long pendant group PHAs are derived.

The PHA polymers may constitute up to 90% of the dry cell weight of bacteria, and are found as discrete granules inside the bacterial cells. These PHA granules accumulate in response to nutrient limitation and serve as carbon and energy reserve materials. Distinct pathways are used by microorganisms to produce each group of these polymers. One of these pathways leading to the short pendant group polyhydroxyalkanoates (SPGPHAs) involves three enzymes, namely thiolase, reductase and PHB synthase (sometimes called polymerase). Using this pathway, the homopolymer PHB is synthesized by condensation of two molecules of acetyl-Coenzyme A to give acetoacetyl-Coenzyme A, followed by reduction of this intermediate to R-3-hydroxybutyryl-Coenzyme A, and subsequent polymerization (FIG. 2a). The last enzyme in this pathway, the synthase, has a substrate specificity that can accommodate C3-C5 monomeric units including R-4-hydroxy acid and R-5-hydroxy acid units. This biosynthetic pathway is found, for example, in the bacteria *Zoogloea ramigera* and *Alcaligenes eutrophus*. The biosynthetic pathway which is used to make the third group of PHAs, the long pendant group polyhydroxyalkanoates (LPGPHAs) is still partly unknown; however, it is currently thought that the monomeric hydroxyacyl units leading to the LPGPHAs are derived by the b-oxidation of fatty acids and the fatty acid pathway (FIG. 2b). The R-3-hydroxyacyl-Coenzyme substrates resulting from these routes are then polymerized by PHA synthases (sometimes called polymerases) that have substrate specificities favoring the larger monomeric units in the C6–C14 range. Long pendant group PHAs are produced, for example, by Pseudomonads.

Presumably, the second group of PHAs containing both short R-3HB units and longer pendant group monomers utilize both the pathways shown in FIGS. 2a and 2b to provide the hydroxy acid monomers. The latter are then polymerized by PHA synthases able to accept these units.

In all, about 100 different types of hydroxy acids have been incorporated into PHAs by fermentation methods (Steinbüchel & Valentin, *FEMS Microbiol., Lett.,* 128:219–28 (1995)). Notably, these include PHAs containing functionalized pendant groups such as esters, double bonds, alkoxy, aromatic, halogens and hydroxy groups.

A preferred polyhydroxyalkanoate for medical applications is poly-4-hydroxybutyrate (P4HB). P4HB is biocompatible, resorbable, processable, strong and ductile. Maintenance of breaking strength is another very important parameter for suturing and stapling materials, especially resorbable ones. As resorbable materials are degraded in vivo, their physical and mechanical properties change as the result of this degradation. For instance, a resorbable suture will loose most of its breaking strength, and as such its ability to fix tissue, more rapidly than the time for its complete resorption. Polyglycolic acid (PGA) sutures, for example, will loose most of their strength within three weeks in vivo (Vet. Surg. 21;192:355–61), but not be completely resorbed before six weeks. This loss of mechanical strength is the result of molecular mass decrease of the polymer. It is important to note that a number of parameters will affect resorption rates and suture breaking strength in vivo, such as type of tissue, mechanical stresses, and the presence of infection.

The examples demonstrate that the degradation rate of P4HB in vivo is fast relative to other PHAs, however, its resorption rate is slower than many of the materials used as resorbable sutures. Additionally, as shown in Table 7, P4HB implants maintain their molecular mass during the process of resorption. This maintenance of molecular mass is expected to be a benefit for the maintenance of mechanical properties, and as such breaking strength of PHAs used as wound closing materials. Because of their excellent mechanical properties, maintenance of high molecular mass, processability, biocompatibility and resorbability, P4HB and P4HB-co-HA are useful in a variety of medical devices, including, for example, resorbable wound closure materials such as suturing and stapling materials, particularly as modified herein to increase their degradation rates.

(2) Sources of PHAs

PHA materials which can be modified to alter their degradation rates can be derived from either a biological source, an enzymatic source, or a chemical source. The biological source can be a microorganism or higher organism such as a plant, and can be derived by genetic engineering.

During the mid-1980's, several research groups were actively identifying and isolating the genes and gene products responsible for PHA synthesis. These efforts lead to the development of transgenic systems for production of PHAs in both microorganism and plants, as well as enzymatic methods for PHA synthesis. Such routes could increase further the available PHA types. These advances have been reviewed in Williams & Peoples, *CHEMTECH,* 26:38–44 (1996) and Williams & Peoples, *Chem. Br.* 33:29–32 (1997).

Methods which can be used for producing PHA polymers suitable for subsequent modification to alter their rates of degradation are described, for example, in U.S. Pat. No. 4,910,145 to Holmes, et al.; Byrom, "Miscellaneous Biomaterials" in *Biomaterials* (Byrom, Ed.), pp. 333–59 (MacMillan Publishers, London 1991); Hocking & Marchessault, "Biopolyesters" in *Chemistry and Technology of Biodegradable Polymers* (Griffin, Ed.), pp.48–96 (Chapman and Hall, London 1994); Holmes, "Biologically Produced (R)-3-hydroxyalkanoate Polymers and Copolymers," in *Developments in Crystalline Polymers* (Bassett Ed.), vol. 2, pp. 1–65 (Elsevier, London 1988); Lafferty et al., "Microbial Production of Poly-b-hydroxybutyric acid" in *Biotechnology* (Rehm & Reed, Eds.) vol. 66, pp. 135–76 (Verlagsgesellschaft, Weinheim 1988); Müller & Seebach, *Angew. Chem. Int. Ed. Engl.* 32:477–502 (1993); Steinbüchel, "Polyhydroxyalkanoic Acids" in *Biomaterials* (Byrom, Ed.), pp. 123–213 (MacMillan Publishers, London 1991); Williams & Peoples, *CHEMTECH,* 26:38–44, (1996); Steinbüchel & Wiese, *Appl. Microbial. Biotechnol.,* 37:691–697 (1992); U.S. Pat. Nos. 5,245,023; 5,250,430; 5,480,794; 5,512,669; and 5,534,432; Agostini, et al., *Polym. Sci.,* Part A-1, 2:2775–87 (1971); Gross, et al., *Macromolecules,* 21:2657–68 (1988); Dubois, et al., *Macromolecules,* 26:4407–12 (1993); Le Borgne & Spassky, *Polymer,* 30:2312–19 (1989); Tanahashi & Doi, *Macromolecules,* 24:5732–33 (1991); Hori, et al., *Macromolecules,* 26:4388–90 (1993); Kemnitzer, et al., *Macromolecules,* 26:1221–29 (1993); Hori, et al., *Macromolecules,* 26:5533–34 (1993); Hocking, et al., *Polym. Bull.,* 30:163–70 (1993); Xie, et al., *Macromolecules,* 30:6997–98 (1997); U.S. Pat. No. 5,563, 239 to Hubbs; U.S. Pat. Nos. 5,489,470 and 5,520,116 to Noda, et al. The PHAs derived from these methods may be in any form, including a latex or solid form.

Identification, cloning and expression of the genes involved in the biosynthesis of PHAs from several microorganisms within recombinant organisms allow for the production of PHAs within organisms that are not native PHA producers. A preferred example is *E. coli* which is a well recognized host for production of biopharmaceuticals and PHAs for medical applications. Such recombinant organisms provide researchers with a greater degree of control of the PHA production process because they are free of background enzyme activities for the biosynthesis of unwanted PHA precursors or degradation of the PHA. Additionally, the proper selection of a recombinant organism may facilitate purification of, or allow for increased biocompatibility of, the produced PHA.

The minimal requirements for the synthesis of PHA in a recombinant organism are a source of hydroxyalkanoyl-CoA and an appropriate PHA synthase (Gerngross & Martin, *Proc. Natl. Acad. Sci.* 92:6279–83(1995)). Recombinant PHA producers thus require a biosynthetic pathway for a hydroxyalkanoyl-CoA monomer and a suitable PHA synthase. Production of a homopolymer requires that the organism produce only one suitable substrate for the PHA synthase, as production of multiple substrates results in the formation of a PHA copolymer. Recombinant organisms containing a transgene encoding a PHA synthase are sufficient for production of P4HB.

In the absence of PHA degradation pathways, the molecular mass of the PHA accumulated in recombinant organisms can be very high. PHB produced in recombinant *E. coli* has been reported to have molecular mass of $4 \times 10^6$ g/mol (Sim, et al., *Nature Biotech.* 15:63–67 (1997)). The molecular mass is important for controlling the physical properties of a given PHA, because the increased molecular mass of PHAs produced in recombinant organisms can lead to improved material properties, such as increased tensile strength and ultimate elongation (Kusaka, et al., *J.M.S. Pure Appl. Chem.* A35:319–35 (1998)).

The biosynthesis of P3HB-co-4HB containing a low level of 4HB (1.5%) has been described in recombinant *E. coli* (Valentin, et al., *J. Biotech.* 58:33–38 (1997)). It is noteworthy that the molecular mass of these PHAs were very high (greater than $1 \times 10^6$ g/mol). Additionally, the biosynthesis of the P3HB-co-4HB and the homopolymer P4HB in recombinant *E. coli* have been described (Hein, et al., *FEMS Microbiol. Lett.*, 153:411–18 (1997)).

In addition to using biological routes for PHA synthesis, PHA polymers may also be derived by chemical synthesis. One widely used approach involves the ring-opening polymerization of β-lactone monomers using various catalysts or initiators such as aluminoxanes, distannoxanes, or alkoxyzinc and alkoxy-aluminum compounds (see Agostini, et al., *Polym. Sci.*, Part A-1, 9:2775–87 (1971); Gross, et al., *Macromolecules*, 21:2657–68 (1988); Dubois, et al., *Macromolecules*, 26:4407–12 (1993); Le Borgne & Spassky, *Polymer*, 30:2312–19 (1989); Tanahashi & Doi, *Macromolecules*, 24:5732–33 (1991); Hori, et al., *Macromolecules*, 26:4388–90 (1993); Kemnitzer, et al., *Macromolecules*, 26:1221–29 (1993); Hori, et al., *Macromolecules*, 26:5533–34 (1993); Hocking & Marchessault, *Polym. Bull.* 30:163–70 (1993). A second approach involves condensation polymerization of esters and is described in U.S. Pat. No. 563,239 to Hubbs, et al. Researchers also have developed chemo-enzymatic methods to prepare PHAs. For example, Xie et al., *Macromolecules*, 30:6997–98 (1997) discloses a ring opening polymerization of beta-butyrolactone by thermophilic lipases to yield PHB.

Biological production of P4HB or P4HB-co-HA has certain advantages over traditional chemical synthetic methods. The chemical synthesis of high molecular mass P4HB (greater than $1 \times 10^5$ g/mol) is difficult due to the tendency of the free acid to lactonize to form the relatively unstrained and kinetically favored five-membered ring. Thus, polycondensation of 4-hydroxybutyric acid is difficult to achieve, while the material that results from high pressure ring-opening polymerization reactions of γ-butyrolactone is of very low molecular mass (Korte & Gelt, *Polymer Lett.*, 4:685 (1966)) and would have poor mechanical properties. An alternate synthetic strategy for P4HB, the free radical ring-opening polymerization of 2-methylene dioxolane, results in a copolymer containing ring opened and unopened units (Bailey, et al. *J. Polym. Sci. Polym. Chem.* 20:3021–30 (1982); Bailey, *J. Polym. Preprints* 25:210–11 (1984)). 4HB has been successfully co-polymerized with 3HB via ring-opening polymerization (Hori, et al., *Polymer* 36:4703–05 (1996)). However, the molecular weight of the copolymers was modest (less than $1 \times 10^5$ g/mol), especially for compositions with more than 80% 4HB (less than $2 \times 10^4$ g/mol). Additionally, many of the catalysts used for the chemical synthesis of polyesters contain toxic metals. These toxic contaminants can be avoided using a biological process to produce PHAs.

(3) PHA Formulations Having Altered Degradation Rates a. Additives Altering Degradation Rates The hydrolysis of polyhydroxyalkanoates is accelerated at acidic or basic pH's and thus the inclusion of acidic or basic additives or excipients can be used to modulate the rate of degradation of PHAs. The excipients can be added as particulates, can be mixed with any other additive or agent incorporated or to be incorporated, or can be dissolved within the polymer. Additives which enhance the rate of degradation include inorganic acids such as ammonium sulfate and ammonium chloride, organic acids such as citric acid, benzoic acids, peptides, ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as polyoxyalkylene based surfactants TWEEN™ and PLURONIC™. The acidic or basic additives can also be nucleophiles or electrophiles. Such additives are preferably used at concentrations between 0.1 and 30% by weight.

The rate of degradation may also be enhanced by additives which form pores or otherwise increase the surface area in the polymer or increase the amorphous content of the polymer. Pore forming agents are generally added as particulates and include water soluble compounds such as inorganic salts and sugars as which are removed by leaching. The pore forming agent can be water absorbing compounds. Suitable particles include salt crystals, proteins such as gelatin and agarose, starches, polysaccharides such as alginate and other polymers. The diameters of the particles may suitably be between nanometers to 500 microns. They may also be lyophilizable. Pore forming agents can be included in an amount of between 0.01% and 90% weight to volume, preferably at a level between one and thirty percent (w/w, polymer), to increase pore formation. For example, in spray drying or solvent evaporation, a pore forming agent such as a volatile salt, for example, ammonium bicarbonate, ammonium acetate, ammonium chloride or ammonium benzoate or other lyophilizable salt, is first dissolved in water. The solution containing the pore forming agent is then emulsified with the polymer solution to create droplets of the pore forming agent in the polymer. This emulsion is then spray dried or taken through a solvent evaporation/extraction process. After the polymer is precipitated, the hardened microparticles are frozen and lyophilized to remove the pore forming agents. Plasticizers, such as the citrate esters, and other polymers like atactic polyhydroxyalkanoates, may be added to increase the amorphous character of the polymer.

Hydrophobic coatings or materials which can be incorporated to increase the degradation rates include hydrophobic compounds such as phospholipids, cholesterol, and other polymers, as well as surfactants. These materials and methods for forming coatings or incorporation into the materials are described in WO 96/18420 by Bracco Research SA, WO 92/18164 by Delta Biotechnology, Ltd., WO 95/03356 by Massachusetts Institute of Technology, PCT/US97/03007 by Acusphere, U.S. Pat. No. 5,271,961 to Mathiowitz, et al., U.S. Pat. No. 5,711,933 to Bichon, et al., and U.S. Pat. No. 5,705,187 to Unger. Specific examples disclose fatty acids and phospholipids as emulsifiers to stabilize the oil phase in the aqueous phase during emulsion/encapsulation process, with the result that the microspheres are coated with an outer layer of the surfactant. The use of additives such as fats, waxes, and high molecular weight hydrocarbon are also disclosed to hydrophobize the polymer walls and to slow water penetration.

b. Modification of PHA Pendant Groups

An alternative method to alter the rate of degradation of PHA polymers involves modification of the polyhydroxyalkanoate pendant groups. The pendant groups may be modified in whole or in part. Pendant groups can, for example, be converted to acidic and basic groups, such as carboxylic acids and amines. These types of groups can enhance degradation by altering local pH values. Alternatively, the pendant groups can be converted to reactive groups, such as alcohols and amines, which can cleave the polymer backbone either by an intramolecular or intermolecular reaction. In addition to these conversions, the pendant groups may also be converted to hydrophilic groups to increase uptake of hydrolytic agents such as water, or they may be converted to groups which would increase the amorphous nature of the polymers. The procedures required to carry out functional group conversion of the pendant groups are well known to those skilled in the art. One suitable method that can be used for preparing a PHA incorporating a unit that alters the degradation rate of the polymer is disclosed in WO 98/39453 by Hein, et al. by which polyhydroxyalkanoates having units containing one, two, or more pendant groups that catalyze PHA degradation or cause chain scission can be readily synthesized. Suitable pendant groups in PHA polymers which will alter the rate of degradation can also be derived directly by fermentation.

c. Chemical Modification of PHAs

The rate of hydrolysis of a polyhydroxyalkanoate depends upon a number of factors. One key factor is the chemical nature or reactivity of the ester linkages between the monomers. The rate of degradation of the PHA backbone can thus be altered by incorporating into the polymer backbone chemical linkages which are more susceptible to hydrolysis, or enzymatic attack. Examples of monomers which can be incorporated into polyhydroxyalkanoate backbones to alter the rate of degradation of the polymer are 2-hydroxy acids, such as glycolic acid and lactic acid, and other hydroxyacids which modulate the reactivity of the ester linkage, such as 2-hydroxyethoxy acetic acid. Besides incorporating other hydroxyacids which yield esters which are more susceptible to hydrolytic or enzymatic attack, other types of functionality bearing one or more heteroatoms may be incorporated into the polymer backbone. For example, one or more of the ester linkages can be replaced by groups such as amide, anhydride, carbonate, or carbamate. Examples of monomers which can be incorporated into the polyhydroxyalkanoate backbone are aminoacids and aminoalcohols. Moreover, multifunctional monomers can be incorporated into the polyhydroxyalkanoate backbones, for example, triols or tetraols. These types of monomer units can also be used to increase or maintain molecular weight of the polymer by interchain crosslinking, or modify crystallinity of the polymers.

A variety of methods may be used to incorporate susceptible chemical linkages into the polyhydroxyalkanoate backbones. For example, co-feeds may be added during fermentation of PHAs which result in the incorporation of desired monomers. Suitable co-feeds include hydroxyalkoxy acetic acids. These types of monomers may also be incorporated during chemical synthesis from hydroxyacid monomers using catalysts, and via coenzyme A derivatives using enzymatic catalysts such as the PHA synthases.

Susceptible chemical linkages may also be incorporated into polyhydroxyalkanoate backbones after their initial synthesis. Methods to accomplish this include chemical transformations such as insertion reactions, irradiation, esterification, transesterification (see, e.g., Otera, et al., *Tetrahedron Lett.*, 27:2383–86 (1986); Otera J. et al., *Org. Chem.*, 56:5307–11 (1991), Otera, et al., *J. Org. Chem.*, 54:4013–14 (1989); and Otera, et al., *J. Chem. Soc. Chem. Commun.* 1742–43 (1991)), ester metathesis reactions (see, e.g., Stanton & Gagné, *J. Am. Chem. Soc.*, 119:5075–76 (1997)), and reactive blending. In the latter case, chemical reactions can be carried out in the melt with a catalyst present. For example, esters or polyesters can be melted with polyhydroxyalkanoates in the presence of suitable catalysts in order to chemically modify the polyhydroxyalkanoate.

d. Processing of PHAs Including Susceptible Linkages

The polyhydroxyalkanoates may be further manipulated using a wide range of polymer processing techniques. Preferred methods for processing these materials include solvent casting, melt processing, fiber processing/spinning/weaving, extrusion, injection and compression molding, and lamination.

III. The Devices and Methods of Manufacture Thereof

The polymer compositions are useful for preparing a variety of biodegradable and/or bioresorbable medical devices, or coatings thereon. The biodegradable polymers preferably exhibit a relatively slow biodegradation, for example, having a in vivo half-life of between three and six months or less. The polymers preferably have a relatively low melting point/glass transition temperature, for example, less than 136° C., and/or are soluble in a non-toxic, non-halogenated solvent, for ease of processing.

Representative devices and applications are described below. State of the art materials in these devices and applications can be replaced totally or partially with the biocompatible polyhydroxyalkanoates described herein to provide the device specifications, such as degradation rate and mechanical properties.

(1) Suture Fastener Devices

These devices are typically used to reattach tissue to bone. Often the procedures involve the attachment of tendon, ligament, or other soft tissue to bones in the shoulder, knee, elbow, wrist, hand, and ankle. In one approach, bone anchors are inserted into the bone and then soft tissue such as ligament or tendon may be sutured to the anchor point. The procedure may be performed in an open manner or preferably using a minimally invasive technique whereby the device is deployed by a suitable delivery device. Examples of suture fastener devices currently in use which are representative of the state of the art include the Bionx Biodegradable Anchor (Bionx Implants, Bluebell, Pa.), BioROC EZ™ Suture Bone Fastener (Innovasive Devices, Marlborough, Mass.), Resorbable Soft Tissue Attachment Device (Zimmer, Warsaw, Ind.) and the Acufex TAG Bioabsorbable Anchors (Smith & Nephew Endoscopy, Mansfield, Mass.). Polyhydroxyalkanoate suture fastener devices can be fabricated according to the methods and procedures described in U.S. Pat. Nos. 5,814,071; 5,797,963; 5,735,875; 5,725,529; 5,649,963; 5,643,321; 5,593,425; 5,423,821; 5,269,809; 5,268,001; 5,163,960; and 5,041,129.

(2) Meniscus Repair Devices

A number of devices exist for the repair of meniscus lesions. In one procedure, these orthopedic fixation devices are used for the secure fixation of longitudinal vertical meniscus lesions (bucket-handle lesions) located in the vascularized area of the meniscus in combination with suitable immobilization. The devices are often used in minimally invasive surgery. Examples of repair devices currently in use which are representative of the state of the art include the BIOFIX™ Meniscus Arrow (Bioscience, Inc., Malvern, Pa.), T-Fix Suture Bar (Acufex Microsurgical, Inc.), and the Meniscal Dart (Innovasive Devices, Marlborough, Mass.). Polyhydroxyalkanoate meniscus repair devices can be fabricated according to the methods and procedures described by de Goot, *Biomaterials*, 18:613–22 (1997), and in U.S. Pat. Nos. 5,855,619; 5,853,746; 5,725,556; 5,645,589; 5,059,206; 5,035,713; 4,976,715; 4,924,865; 4,895,148; and 4,884,572.

(3) Rivets and Tacks

Biodegradable rivets and tacks can be used in soft tissue reattachment. Particular uses include the reattachment of soft tissue in the shoulder, including instability repairs in the shoulder (Bankart procedures), SLAP lesion repair, acromio-clavicular separation repairs, rotator cuff repairs, capsular shift or capsulolobral reconstructions, biceps tenodesis, and deltoid repair. An example of the state of the art rivet device is the LactoSorb Pop Rivet (Biomet, Inc., Warsaw, Ind.). Polyhydroxyalkanoate rivet and tack devices can be fabricated according to the methods and procedures described by Speer, et al, *Clin. Orthop.* 291:67–74 (1993), and U.S. Pat. Nos. 5,840,078; 4,895,148; 5,868,747; 5,843,084; 5,840,078; 5,827,298; 5,807,292; 5,785,713; 5,730,744.

(4) Staples

Biodegradable staples can be used for the fixation of soft tissues. Such staples can be used, for example, to repair vertical longitudinal full thickness tears (i.e. bucket-handle) of the meniscus. An example of such state of the art devices include the Absorbable Implantable Staple (United States Surgical Corporation, Norwalk, Conn.). Polyhydroxyalkanoate staples can be fabricated according to the methods and procedures described by U.S. Pat. Nos. 5,728,116; 5,423,857; 5,345,949; 5,327,914; 5,222,963; 4,889,119; 4,741,337; 4,646,741; 3,797,499; and 3,636,956.

(5) Screws

Biodegradable screws, including interference screws, can be used in the fixation of soft tissue. Such screws can be used, for example, to fix soft tissue grafts to bone during cruciate ligament reconstruction surgeries of the knee. Examples of such state of the art screws include the RCI screw (Smith & Nephew, Carlsbad, Calif.) and the Arthrex BIO-INTERFERENCE™ Screw (Arthrex, Naples, Fla.). Polyhydroxyalkanoate screws can be fabricated according to the methods and procedures described in U.S. Pat. Nos. 5,275,601; 5,584,836; 5,364,400; 5,348,026; 5,876,455; 5,632,748; 5,496,326; 5,718,706; 5,690,222; 5,383,878; 5,425,733; 5,417,692; 4,927,421; 5,211,647; 5,116,337; and 4,927,421.

(6) Bone Plates and Bone Plating Systems

Biodegradable fixation systems consisting of plates, plates and mesh, and mesh, in varying configurations and length, can be attached to bone for reconstruction. Such uses include the fixation of bones of the craniofacial and midfacial skeleton affected by trauma, fixation of zygomatic fractures, or for reconstruction. The plates may also be contoured by molding. Examples of such state of the art devices include the Howmedica LEIBINGER™ Resorbable Fixation System (Howmedica, Rutherford, N.J.), and the LACTOSORB™ Trauma Plating System (Biomet, Inc., Warsaw, Ind.). Polyhydroxyalkanoate bone plates and bone plating systems can be fabricated according to the methods and procedures described by U.S. Pat. Nos. 5,853,746; 5,735,875; 5,725,529; 5,717,030; 5,662,710; 5,626,611; 5,578,046; 5,373,860; 5,092,883; 4,988,358; 4,683,878; and 3,997,138.

(7) Surgical Mesh

Biodegradable surgical mesh may be used in general surgery. For example, surgical meshes are used in the treatment of hernias where the connective tissue has ruptured or as a sling material to support the repositioning and support of the bladder nect for female urinary incontinence. Such meshes (plugs) may also be used as soft tissue implants for reinforcement of soft tissue, for example, in the repair of abdominal aponeuroses and the abdominal wall, fascial and capsular defects, and patellar and achilles tendons, and replacement of infraspinatus thedons and cranial cruciate ligaments. Other uses include the bridging of fascial defects, as a trachea or other organ patch, organ salvage, slings (including an intestinal sling), dural grafting material, wound or burn dressing, and as a hemostatic tamponade. Examples of such state of the art meshes include the Brennen Biosynthetic Surgical Mesh Matrix (Brennan Medical, St. Paul, Minn.), GORE-TEX™ Patches (Gore, Flagstaff, Ariz.), and SEPRAMESH™ (Genzyme Corporation, Mass.). Polyhydroxyalkanoate surgical meshes can be fabricated according to the methods and procedures described by Bupta, "Medical textile structures: an overview" *Medical Plastics and Biomaterials*, pp. 16–30 (January/February 1998) and by methods described in U.S. Pat. Nos. 5,843,084; 5,836,961; 5,817,123; 5,747,390; 5,736,372; 5,679,723; 5,634,931; 5,626,611; 5,593,441; 5,578,046; 5,516,565; 5,397,332; 5,393,594; 5,368,602; 5,252,701; 4,838,884; 4,655,221; 4,633,873; 4,441,496; 4,052,988; 3,875,937; 3,797,499; and 3,739,773.

(8) Repair Patch

Biodegradable repair patches may be used in general surgery. For example, these patches may be used for pericardial closures, the repair of abdominal and thoracic wall defects, inguinal, paracolostomy, ventral, paraumbilical, scrotal, femoral, and other hernias, urethral slings, muscle flap reinforcement, to reinforce staple lines and long incisions, reconstruction of pelvic floor, repair of rectal and vaginal prolapse, suture and staple bolsters, urinary and bladder repair, pledgets and slings, and other soft tissue repair, reinforcement, and reconstruction. Examples of such state of the art patches include the TISSUEGUARD™ product (Bio-Vascular Inc., St. Paul, Minn.). Polyhydroxyalkanoate repair patches can be fabricated according to the methods and procedures described in U.S. Pat. Nos. 5,858,505; 5,795,584; 5,634,931; 5,614,284; 5,702,409; 5,690,675; 5,433,996; 5,326,355; 5,147,387; 4,052,988; and 3,875,937.

(9) Sling

Biodegradable slings can be used as implants to reinforce soft tissue where weakness exists. Examples of such procedures include pubourethral support and bladder support, urethral and vaginal prolapse repair, reconstruction of the pelvic floor, and sacro-colposuspension. The device can be used to treat female urinary incontinence resulting from urethral hypermobility or intrinsic sphincter deficiency. Examples of such state of the art devices include the Mentor SUSPEND™ Sling (Mentor Corporation, Minneapolis, Minn.). Polyhydroxyalkanoate sling devices can be fabricated according to the methods and procedures described in U.S. Pat. Nos. 5,700,479; 5,860,425; 5,836,315; 5,836,314; 5,813,408; 5,690,655; 5,611,515; 4,217,890.

(10) Cardiovascular Patch

Biodegradable cardiovascular patches may be used for vascular patch grafting, (pulmonary artery augmentation), for intracardiac patching, and for patch closure after endarterectomy. Examples of similar state of the art (non-degradable) patch materials include Sulzer Vascutek FLUO- ROPASSIC™ patches and fabrics (Sulzer Carbomedics Inc., Austin, Tex.). Polyhydroxyalkanoate cardiovascular patches can be fabricated according to the methods and procedures described in U.S. Pat. Nos. 5,716,395; 5,100,422, 5,104,400; and 5,700,287; and by Malm, et al., *Eur. Surg. Res.,* 26:298–308 (1994).

(11) Sutures

Biodegradable sutures are used generally for soft tissue approximation where only short term wound support is required. Examples of similar state of the art devices include VICRYL RAPIDE™ (Ethicon, Inc., Somerville, N.J.). Polyhydroxyalkanoate suture devices can be fabricated according to the methods and procedures described in Wound Closure Biomaterials and Devices, (Chu, et al., Eds.) CRC Press, Boca Raton, Fla., 1996.

(12) Orthopedic Pins

Biodegradable pins, including bone filling augmentation material, are used for bone and soft tissue fixation. Such devices have been used, for example, to stabilize wrist, foot, ankle, hand, elbow, shoulder and knee fractures. Examples of such state of the art devices include the BIOFIX™ Biodegradable Fixation Rod (Davis & Geck, Danbury, Conn.), ORTHOSORB™ pins (Johnson & Johnson, New Brunswick, N.J.) and the RESOR-PIN™ Resorbable Membrane Pin (Geistlich-Pharma, Washington, D.C.). Polyhydroxyalkanoate orthopedic pins can be fabricated by conventional processing techniques such as melt processing techniques like injection and compression molding, fiber forming, as well as solvent based techniques.

(13) Adhesion Barriers

Biodegradable adhesion barriers are used in general surgery to prevent undesirable adhesions, particularly following surgery. Examples of such state of the art devices used for these purposes include the Endopath INTERCEED™ Absorbable Adhesion Barrier (Ethicon, Inc.), and SEPRAFILM™ (Genzyme, Cambridge, Mass.). Polyhydroxyalkanoate adhesion barriers can be fabricated according to the methods and procedures described in U.S. Pat. Nos. 5,824,658; 5,795,584; 5,791,352; 5,711,958; 5,639,468; 5,626,863; 5,626,622; 5,607,686; 5,580,923; 5,137,875, and 4,840,626.

(14) Stents

Stents are currently used in a range of medical applications, normally to prevent reocclusion of a vessel. Examples include cardiovascular and gastroenterology stents. Generally these stents are non-degradable. Ureteric and urethral stents are used to relieve obstruction in a variety of benign, malignant and post-traumatic conditions such as the presence of stones and/or stone fragments, or other ureteral obstructions such as those associated with ureteral stricture, carcinoma of abdominal organs, retroperitoneal fibrosis or ureteral trauma, or in association with Extracorporeal Shock Wave Lithotripsy. The stent may be placed using endoscopic surgical techniques or percutaneously. Examples of state of the art stents include the double pigtail ureteral stent (C.R. Bard, Inc., Covington, Ga.), SpiraStent (Urosurge, Coralville, Iowa), and the Cook Urological Ureteral and Urethral Stents (Cook Urological, Spencer, Ind.).

One advantage of polyhydroxyalkanoate stents is their bioabsorbability, which is particularly desirable in applications such as urological applications, since a second procedure is not required to remove the stent. Furthermore, one of the main problems in using metallic stents in cardiovascular applications is the subsequent restenosis caused by excessive growth of the endothelial wall, which is believed due, at least in part, to irritation caused by the metallic stent on the vessel wall (see Behrend, *American J. Cardiol.* p. 45, TCT Abstracts (October 1998); Unverdorben, et al., *American J. Cardiol.* p. 46, TCT Abstracts (October 1998)). A bioabsorbable stent made from, or coated with a polyhydroxyalkanoate should produce reduced or no irritation.

Polyhydroxyalkanoate stents can be fabricated according to the methods and procedures described in U.S. Pat. Nos. 5,792,106; 5,769,883; 5,766,710; 5,670,161; 5,629,077; 5,551,954; 5,500,013; 5,464,450; 5,443,458; 5,306,286; 5,059,211, and 5,085,629. See also Tanquay, *Cardiology Clinics,* 23:699–713 (1994) and references therein, and Talja, *J. Endourology,* 11:391–97 (1997).

(15) Guided Tissue Repair/Regeneration

Guided tissue regeneration is a periodontal procedure wherein a membrane is placed over bone and root surfaces of a surgically exposed area. The membrane acts as a barrier isolating the healing bone and periodontal ligament from the gum, giving the slower-growing bone and ligament cells an opportunity to regenerate. The ultimate goal is to strengthen the attachment of the tooth to the jawbone, thereby providing improved chances of preserving the tooth or teeth. Examples of state of the art membranes that are used in the procedure include GUIDOR™ (Procordia Oratech A.B., Sweden), Gore Resolut XT™ (W.L. Gore & Associates, Flagstaff, Ariz.), VICRYL™ Periodontal Mesh (Ethicon, Sommerville, N.J.), and ATRISORBυ Bioabsorbable GTR barrier (Atrix Laboratories, Ft. Collins, Colo.). Polyhydroxyalkanoate guided tissue repair barriers may be fabricated according to methods described in U.S. Pat. Nos. 5,853,746; 5,736,152; 5,543,441; 5,508,036; 5,455,041; 5,368,859; 5,077,049; 5,278,201; 5,250,584; 5,077,049; and 4,938,763.

(16) Articular Cartilage Repair

Biodegradable polymer matrices, alone or incorporating cell and/or bioactive molecular growth factors, have been used to repair articular cartilage defects. An example of a material used in such a procedure is polylactic acid (Schroder, et al., *J Biomed. Mat. Res.,* 25:329–39 (1991)). Polyhydroxyalkanoate articular cartilage repair devices can be fabricated according to the methods and procedures described in U.S. Pat. Nos. 5,876,452; 5,736,372; 5,716,981; 5,700,774; 5,655,546; and 5,041,138.

(17) Nerve Guides and Tendon Repair

Biodegradable devices may be used as guides to facilitate the regrowth and reconnection of severed or damaged nerves and tendons. The devices are generally fabricated as tubes. An example of a nerve guide is the Neurotube™ product. Polyhydroxyalkanoate tendon repair devices may be prepared according to procedures described in U.S. Pat. No. 4,792,336. Polyhydroxyalkanoate nerve guides can be fabricated according to the methods and procedures described in U.S. Pat. Nos. 5,800,544; 5,735,863; 5,584,885; 5,514,181; 5,026,381; 5,019,087; and 4,955,893.

(18) Atrial Septal Defect Repair

Large atrial septal defects that cannot be closed directly with sutures can be repaired with pericardial patches or with synthetic non-absorbable materials. Polyhydroxyalkanoate atrial septal defect repair patches and devices can be fabricated according to the methods and procedures described in U.S. Pat. Nos. 5,853,422; 5,634,936; 5,861,003; 5,855,614; and by Malm, T. et al., *Scand. J. Thor. Cardiovasc. Surg.,* 26:9–14 (1992).

(19) Pericardial Patch

Reoperation after open heart surgery is often made more difficult due to adhesions. Prevention of adhesions through pericardial substitution is therefore becoming more desirable. Many different types of materials have been used as pericardial patches including silicone membranes, polyurethane, fascia lata, Gore-Tex™, pericardium xenografts, dura mater and siliconized Dacron™. Pericardial patches derived from polyhydroxyalkanoates may be derived according to methods described by Gabbay, *Ann. Thorac. Surg.,* 48:803–12 (1989); Heydorn, *J. Thorac. Cardiovasc. Surg.,* 94:291–96 (1987), and U.S. Pat. Nos. 5,713,920; 5,468,253; and 5,141,522.

(20) Bulking and Filling Agents

Bulking agents are commonly used in plastic surgery to fill in defects, and also in the treatment of adult incontinence where they are used as sphincter bulking materials. An example of such a material is collagen. Polyhydroxyalkanoate bulking and filling devices can be fabricated according to the methods and procedures described in U.S. Pat. Nos. 5,376,375; 5,702,715; 5,824,333; 5,728,752; 5,599,852; 5,785,642; 5,755,658; and 5,728,752.

(21) Vein Valves

Venous leg ulcers occur on the lower leg and are caused by venous insufficiency, or poorly functioning valves in the veins of the legs. Currently, there is no treatment available to repair defective vein valves. Instead, only the ulcers are treated at an estimated average cost of $2,700 per patient per year (for the estimated 600,000 patients suffering from venous leg ulcers). It would therefore be desirable to provide replacement vein valves, which preferably can be implanted by a minimally invasive means, or by routine surgery. Vein valves can be derived from polyhydroxyalkanoate polymers, wherein these polymers are fashioned into a valve structure. The polymers may be used alone, coated, or modified with another agent, such as a biological factor. They may be combined with other materials, and/or made porous. Alternatively, the polymers may be fashioned into scaffolds which can optionally be cell seeded prior to implantation. Suitable methods to prepare valves and seed tissue engineered scaffolds are described in Breuer et al., *Biotechnology and Bioengineering,* 50:562–67 (1996); Niklason et al., *Science,* 284:489–93 (1999); and *Principles of Tissue Engineering* (Lanza, et al., Eds.) Academic Press, Austin, 1997.

(22) Bone Marrow Scaffolds

A number of different surgical procedures employ bone marrow transplants. In many cases, bone marrow is taken from the iliac crest and used at another location to aid in the repair of tissues and organs, usually bone. Examples include the use of bone marrow in the repair of bone fractures, such as a tibial plateau fracture, spinal procedures, as well as treatment of abnormalities in the maxillofacial and craniofacial regions requiring surgery. In certain cases, large amounts of bone marrow are required for these procedures, but the amount of bone marrow available is limited, particularly in young and small patients. It therefore is desirable to provide a method which allows the amount of available bone marrow to be utilized effectively over a greater portion of the surgical site, and/or at additional sites, without losing any of its desirable properties for repair and regeneration. It also may be desirable to provide the bone marrow in a more useful form for subsequent surgical use.

The effective coverage or placement of useful bone marrow can be increased by mixing, seeding, or combining the bone marrow with a porous polyhydroxyalkanoate polymer. The latter scaffold could be prepared, for example, by a salt leaching technique described in *Principles of Tissue Engineering* (Lanza, et al., Eds.) Academic Press, Austin, 1997. After harvesting, the bone marrow is taken up into the desired polyhydroxyalkanoate scaffold by, for example, applying suction or pressure, or by other means. The polyhydroxyalkanoate scaffold also can comprise other materials, such as bioactive agents, other polymers, or calcium phosphate, and can be shaped or molded for a particular use. The scaffold containing the bone marrow may then be applied to the desired surgical sites.

(23) Meniscus Regeneration

An unmet need in meniscus repair relates to defects located in the avascular region of the menisci where no blood vessels are present. Tears or defects in this region are not expected to heal. The only available treatment for avascular tears is a meniscectomy, where the portion of the meniscus surrounding the tear is removed. This procedure is unsatisfactory, as the meniscectomy disturbs the ability of the meniscus to function properly. Therefore, a meniscus regeneration product able to facilitate repair of avascular tears is highly desirable.

Certain polyhydroxyalkanoates have desirable properties for use as a meniscus regeneration template. These properties include elasticity, flexibility, appropriate compressive strength, and controlled bioabsorption rates. The regeneration template could also incorporate growth factors and/or cells. Polyhydroxyalkanoate meniscus regeneration devices can be fabricated using a variety of different processing techniques, including the use of salt leaching, melt, solvent, fiber, and foam processing techniques. Devices may be formed, for example, as sponges, foams, non-wovens materials, woven materials. Suitable methods for fabricating polyhydroxyalkanoate meniscus regeneration templates are described by Widmer & Mikos, "Fabrication of biodegradable polymer scaffolds for tissue engineering" in *Frontiers in Tissue Engineering* (Patrick, et al., Eds.) Ch. II.5, pp.107–20 (Elsevier Science, New York, 1998).

(24) Ligament and Tendon Grafts

The anterior cruciate ligament (ACL) is a broad, thick cord, about the size of a person's index finger, which is essential for guiding the tibia (shinbone) in a normal path along the end of the femur (thighbone) and maintaining stability of the knee joint. When this ligament is torn or ruptured, the joint loses stability and further destruction of the articular and meniscal cartilage results, i.e. degenerative arthritis. The serious injury often results from a sporting accident and usually requires surgical repair or reconstruction. The most common reconstruction of the ACL involves the use of patellar tendon and hamstring grafts, with cadaver grafts representing a third option. (Suturing is sometimes an option, but 50% of these procedures are reported to fail because of the strain placed on the knee.) The patellar graft is usually harvested with a piece of the patient's patella (knee cap) bone along with a piece of bone from where the patellar tendon inserts into the tibia. It is considered to be a strong donor material, but can increase sensitivity of the patella and tibia where the bone is removed. The hamstring graft is taken from tendons on the inner side of the knee which does not interfere with the patella and tendon; however, this graft is weaker than the patellar graft.

A device known as a ligament augmentation device (LAD) was introduced for these reconstructive procedures when it was observed that biological grafts undergo a period of degeneration and loss of strength before being incorporated. The LAD is meant to function to protect the graft during this vulnerable phase, and has been shown to share loads in composite grafts, increasing the strength of the ligament graft by as much as 50%. However, current devices are thought to induce inflammatory responses in the knee, so their routine use in uncomplicated reconstructions has been limited.

Polyhydroxyalkanoate polymers can be used to fabricate bioabsorbable LADs and other ligament and tendon graft devices. The advantages of these devices rests in their improved biological response combined with their ability to provide early strength to the autograft. Suitable devices can be fabricated, for example, by processing the polyhydroxyalkanoates into fibers to be used alone, or after further modification into braided or multi-filament forms. Suitable methods for preparing these devices with polyhydroxyalkanoates are described in U.S. Pat. No. 4,792,336 to Hlavacek, et al.

(25) Bone Graft Substitute

About 500,000 surgical operations annually require the use of bone grafts, for example, in spinal fusions, trauma fractures, and in periodontal surgery. In a typical procedure, bone graft material is harvested surgically from the patient's own hipbone and then inserted into the grafting site where bone regrowth is desired. The graft material contains a variety of bone promoting agents which help stimulate the formation of new bone and healing. This procedure frequently provides good results, but undesirably requires a second operation to harvest the autograft. To avoid the harvesting procedure, surgeons may use other types of bone graft substitutes including cadaver bone products and composites containing calcium phosphate and calcium carbonate. The latter materials generally do not perform well, and disease transmission issues always accompany the use of cadaver-derived materials.

For these reasons, significant efforts are underway to develop new bone graft substitutes based on the use of osteoconductive (bone scaffolding) and/or osteoinductive (new bone from biological stimulation) materials. It has become increasingly apparent that these materials require a carrier vehicle for optimum performance. Polyhydroxyalkanoate polymers can be used as carrier vehicles. Such devices may be fabricated according to procedures described by Widmer & Mikos, "Fabrication of biodegradable polymer scaffolds for tissue engineering" in *Frontiers in Tissue Engineering* (Patrick, et al., Eds.) Ch. II.5, pp. 107–20 (Elsevier Science, New York, 1998); Damien, et al., *J. Appl. Biomater.* 2(3):187–208 (1991); and Gugala, et al., *J. Orthop Trauma,* 13(3):187–95 (1999).

(26) Skin Substitutes

Skin loss due to either burns or ulcers is a major medical problem. In severe cases, treatment frequently employs autografts which are taken from the patient. However, this source of skin is limited, and the procedure results in additional morbidity and scarring. A potential solution to these problems lies in the development of human skin substitutes based upon cell seeded, or tissue engineered, matrices. The matrices may be derived from bioabsorbable polymers such as polyhydroxyalkanoate polymers, which can provide a wide range of properties and fabrication options needed to produce suitable skin substitutes. For example, advantages of polyhydroxyalkanoates in these products include the stability of the polyhydroxyalkanoate matrix to cell culture, improved wound healing due to the use of a less inflammatory matrix material, and ease of use, such as flexibility and suturing. Polyhydroxyalkanoate polymers may be fabricated into suitable matrices for use as skin substitutes using procedures described by Widmer & Mikos, "Fabrication of biodegradable polymer scaffolds for tissue engineering" in *Frontiers in Tissue Engineering (Patrick, et al., Eds.) Ch. II.5*, pp.107–20 (Elsevier Science, New York, 1998).

(27) Dural Substitutes

Following neurosurgical operations, cadaveric dura mater grafts have commonly been used to repair dural defects. However, because of the risk of transmitting Creutzfeldt-Jakob disease through these grafts, the World Health Organization has recommended that cadaveric dural grafts no longer be used. Although polytetrafluoroethylene can be used as an alternative permanent synthetic material for dural repair, concerns relating to the material's biocompatibility have been raised, increasing interest in the development of a bioabsorbable dural substitute. Polyhydroxyalkanoates with appropriate flexibility and strength can be processed into devices suitable for use as dural substitutes. These devices may take the form of porous materials, and can be derived for example from porous polyhydroxyalkanoate matrices, and/or polyhydroxyalkanoate fibers processed into webs, non-woven or woven fabrics. Widmer & Mikos, "Fabrication of biodegradable polymer scaffolds for tissue engineering" in *Frontiers in Tissue Engineering (Patrick, et al., Eds.) Ch. II.5,* pp.107–20 (Elsevier Science, New York, 1998); and Yamada, et al.,*J. Neurosurg.* 86:1012–17 (1997).

(28) Ocular Cell Implants

Two monolayers of cells, known as retinal pigment epithelium and corneal endothelium are essential for normal vision. In age-related macular degeneration, the function of the retinal pigment epithelium is believed to be altered leading to visual loss. Replacement of this altered epithelium with a healthy retinal pigment epithelium can potentially provide a treatment for this debilitating condition. Transplantation of donor cell suspensions has been attempted but is problematic, and has lead to several attempts to use synthetic bioabsorbable polymers and protein polymers as tissue engineering scaffolds to deliver retinal pigment epithelium and corneal endothelium into the eye. Polyhydroxyalkanoates can be used as scaffolds to deliver these cells, and monolayers derived therefrom, into the eye. They can be processed into suitably sized scaffolds (specifically very thin yet strong constructs), and do not produce acidic byproducts, like some of the commercially available bioabsorbable synthetic polymers, which can be deleterious to cell viability and function. Furthermore the polyhydroxyalkanoate materials can be fabricated into appropriate scaffold devices with desirable mechanical and handling properties. Suitable methods to prepare polyhydroxyalkanoate ocular cell implant devices are described in Hadlock et al., *Tissue Engineering,* 5:187–96 (1999), and additional methods to produce other suitable tissue engineering scaffolds are described in Widmer & Mikos, "Fabrication of biodegradable polymer scaffolds for tissue engineering" in *Frontiers in Tissue Engineering* (Patrick, et al., Eds.) Ch. II.5, pp. 107–20 (Elsevier Science, New York, 1998); and, Yamada, et al., *J. Neurosurg.* 86:1012–17 (1997).

(29) Spinal Fusion Cages

Spinal fusion cages are used to treat various forms of degenerative disc disease, a condition in which the spinal discs, located between each vertebra, are no longer able to cushion and protect the vertebra during movement. This can result in severe, and occasionally, crippling back pain, as the vertebrae rub against adjacent spinal nerves. The condition results from the wearing down of the shock absorbing cartilage that separates the vertebrae of the spine, and can be due to aging or injury. Degenerating discs also become dehydrated losing height, and thereby bringing the vertebrae closer together.

Degenerative disc disease can be treated surgically after other therapies fail to provide relief. Surgical procedures known as discectomy or laminectomy are sometimes employed to remove the tissue that is causing pain. The ultimate surgery is spinal fusion, wherein the affected area of the vertebrae is disabled or immobilized eliminating the movement that is responsible for causing the pain. The traditional spinal fusion procedure used to involve the use of bone graft material, with or without pedicle screws and plates, to fuse adjacent vertebrae together. However, this procedure is traumatic, causes significant muscle damage, meaningful loss of blood, and a long, sometimes painful, recovery period. Increasingly surgeons are using a relatively new procedure involving spinal fusion cages to fuse two or more vertebrae into one stable bony mass. In this procedure, a cage which comprises a hollow cylinder is implanted in the disc space, following removal of the defective disc, and packed with bone graft material. Fusion occurs as new bone grows into the fusion cages through holes in the cylinder. The cages also serve to restore disc space height while the spine heals. Typically, a surgeon may employ two cages side by side in a procedure, and importantly, the procedure can be performed through small incisions either through the front or back of the patient. The procedure has great benefits, allowing the surgeon a way to avoid cutting important back muscles and having to reposition the delicate spinal chord. Recovery rates are faster, better fusions and outcomes are achieved, and less blood loss occurs during the procedure.

Polyhydroxyalkanoates can be fabricated into spinal fusion cages or cage parts using conventional processing techniques such as melt, solvent, and fiber processing. The advantages of using polyhydroxyalkanoates in this application would be their ability to serve as transitional constructs providing the initial stability required prior to the formation of a stable fusion, yet bioabsorbing when they are no longer needed—eliminating the presence and potential dangers of a foreign object in the body. Resorption of the polyhydroxyalkanoate also would ensure that full weight bearing is transferred to the spine and fusion site, helping to prevent any subsequent resorption of bone, loss of strength, instability, or movement of the fusion device. This can be achieved either by making a spinal cage completely from polyhydroxyalkanoate polymers, blends, or composites of other materials, or by incorporating into such a device a polyhydroxyalkanoate component that transfers stress and strain away from the fusion cage and onto the spine as the component bioabsorbs. The component can be, for example, a rod, washer, screw, pin, strut, plate, staple, or a combination of such elements. Devices can also be fabricated from polyhydroxyalkanoates which would be expected to provide improved results, particularly by promoting new bone growth formation. These devices could incorporate fusion promoting substances in the polymer which is not readily achieved with the current metal fusion cages and devices. The polymers can also be configured in porous and non-porous forms. Designs and methods which can be used to prepare polyhydroxyalkanoate spinal cages are disclosed in U.S. Pat. Nos. 5,895,426; 4,936,848; 4,961,740; 5,910,315; 5,645,598; 4,743,236; 5,665,122; and 5,910,315.

(30) Wound Dressing Agents and Hemostats

Polyhydroxyalkanoates can be used to fabricate wound dressings and hemostat devices. There are several properties that dressing materials for wounds ideally should possess, including an ability to remove excess exudate from the wound, protect the wound from mechanical injury, and reduce the risk of infection. The wound dressing must be free of toxic substances, and it should not adhere to the wound which would disturb the healing process. Commonly used dressings include cellulosic dressings such as cotton lint, cotton gauze, cotton wool pads, cotton/rayon wool pads faced with non-woven materials. Other dressings contain polyurethanes, polyurethane-polyols, and/or natural polysaccharide or protein polymers such as collagen. These dressings may be impregnated, coated, or otherwise contain agents such as alginates which raise the absorptive capacity of the dressing and can stimulate the clotting cascade for bleeding wounds, and/or other agents such as silver salts, antiseptics, analgesics, and/or preservatives. The dressings may be prepared, for example, as fiber mats, sponges, foams, nets, fibrous substrates. The dressings can be prepared to have a range of different pore sizes and densities. The dressings can be used in the treatment of a variety of wound types, including pressure sores, decubitus ulcers, venous stasis ulcers, infected wounds, deep and open surgical wounds and incisions, sealing of percutaneous incisions or punctures, and burns.

The advantages of using the polyhydroxyalkanoate polymers in these wound dressing and hemostat applications include the ability to provide a microclimate, and/or a tissue scaffold, for tissue regeneration. It is possible to produce wound dressings and hemostats that bioabsorb in vivo, because the polyhydroxyalkanoates are bioabsorbable. Alternatively, non-absorbable dressings, particularly for external application, can be prepared. Wound dressings may be prepared from polyhydroxyalkanoate polymers that are comfortable, flexible, and absorbent. They may be prepared, for example, as fiber mats, sponges, foams, nets, fibrous or porous forms, and can have a range of pore sizes and densities. The PHA wound dressings and hemostats also can be prepared to include other agents such as alginates, silver salts, antiseptics, analgesics, and preservatives. The hydrophobicity, hydrophilicity, absorption capacity, surface properties, and mechanical properties of the wound dress or hemostat can be modified, for example, by varying the nature of the monomer hydroxy acids incorporated into the polymer. It is also possible to incorporate polyols into the polyhydroxyalkanoate polymers to change these properties. Such methods are described, for example, in PCT WO 97/07153 and U.S. Pat. No. 5,994,478. The polyhydroxyalkanoates also may be used as a component of a wound dressing or hemostat device, for example, with a polyurethane or collagen material. Examples of suitable methods for preparing wound dressing devices and hemostats are described in U.S. Pat. Nos. 3,978,855; 4,664,662; 5,021,059; 5,676,689; 5,861,004; and 5,914,125.

(31) Bone Dowel Devices

Polyhydroxyalkanoates can be fashioned into dowels for spinal or other orthopedic repair. Bone dowels are commonly used in spinal fusion procedures for a variety of reasons, for example, to treat patients with degenerative disc disease, deformities, as well as those involved in traumatic injuries. In posterior fusions, bone is typically removed from the hip area and placed in a traverse direction between adjacent vertebrae, often with the aid of spinal instruments. The instrument helps to hold the spine together so that a bone fusion can occur. Fusions in the lumbar area also can be done anteriorly, wherein the disc is removed and bone graft is placed between the two adjacent vertebral bodies. Other procedures employ a threaded bone dowel which is typically a piece of cadaver donor bone that has been machined into a screw configuration and can be hollowed out to form a cage. The bone dowel is then filled with a small amount of bone from the patient's hip. A tapping device is then used to create screw threads in the vertebral bodies that will be fused by the bone dowel. The bone dowel is then screwed into place between the vertebrae.

Polyhydroxyalkanoates can be made into these dowels, which can take the form of hollowed constructs able to receive bone graft and be placed between vertebrae, as well as composite dowel constructs. The key advantages of using polyhydroxyalkanoates to construct these devices is their ability to provide the transitional support (e.g., mechanical support) necessary during formation of a stable fusion, coupled with their ability to completely resorb, thereby transferring full weight bearing to the spine in a manner able to prevent, or at least minimize, loss of bone mass and strength, and prevent subsequent movement in the fusion area. The polyhydroxyalkanoate bone dowels can be used or without additional hardware, or can be incorporated into such hardware, particularly in a manner that allows weight bearing to be subsequently transferred from the hardware to the spine upon resorption of the polyhydroxyalkanoate component. The dowels can be formed, for example, by using conventional polymer processing techniques with molds and/or machining methods. The dowels may be threaded, porous or non-porous, as desired. If necessary, x-rays and CT scans can be used in the fabrication process to custom make the dowel for patients. Examples of bone dowels and applications therefor are described in U.S. Pat. Nos. 4,501, 269; 5,015,255; 5,522,894; and 5,860,973.

The polyhydroxyalkanoates also can be used to improve the biocompatibility of other devices and tissue engineering constructs. For example, a polyhydroxyalkanoate coating can be coated onto devices or constructs formed of less biocompatible materials.

(32) Heart Values and Vascular Grafts

The unidirectional flow of blood through the entire circulatory system is controlled by the heart's valves. Humans have a total of four heart valves: the tricuspid valve, the pulmonary valve, the mitral valve, and the aortic valve. With the exception of the mitral valve which has just two cusps (or leaflets), each valve has three cusps which are forced open and shut by differences in pressure within the heart. Valvular heart disease, which is characterized by a defective heart valve, impairs the ability of the heart to function properly. This can be caused by degenerative processes, congenital defects, bacterial endocarditis, or rheumatic fever, and results in oscillations of a patient's blood pressure and circulation, leading to heart murmurs, heart failure, or myocardial infarction (insufficient blood flow to heart muscle).

Currently, there are a number of different methodologies employed to treat heart valve disease, including drug treatments, valve repair and valve replacement. In non-life threatening situations, drugs used in the treatment of congestive heart failure are usually employed first to make the heart work harder and pump blood throughout the body. However, once valvular disease progresses to the point at which the heart's ability to pump blood is significantly impaired, surgery is usually recommended to repair or replace the diseased valve. Many surgeons prefer to repair a heart valve when possible; however, in many cases this is either not possible or the benefits are short lived.

Valvular replacement surgery is a traumatic procedure which involves placing a patient on cardiopulmonary bypass while the diseased valve is replaced with an artificial valve prosthesis. There are currently two primary types of artificial valve prostheses: mechanical heart valves and tissue heart valves. Each type has benefits and drawbacks. Mechanical valves, for example, are noted for their durability and reliability. However, a major drawback is the need for the recipient to be placed upon a lifelong anticoagulant therapy which involves continuous monitoring of anticoagulant levels. Current tissue valves, derived from heterologous sources (cows and pigs), on the other-hand, do not require anticoagulant therapy, they are quiet, provide physiological flow patterns, and typically have slowly developing rather than catastrophic failure modes. The major problem associated with these valves is their lack of durability. Most of the current tissue valves generally last between five and fifteen years before they need to be replaced due to a gradual deterioration of the (non-living) tissue. Most experts agree that if the durability problem can be solved, tissue valves would be the clear choice for treatment of valvular heart disease, as no synthetic material has proven to have the properties needed to endure bidirectional flexing some 40 million times a year without producing thrombosis. Furthermore, mechanical valves cannot be used to repair valve leaflets. One potential solution which could address the deficiencies of current valve replacements is to develop a tissue engineered heart valve. The valve would initially comprise a heart valve scaffold material which could be seeded with appropriate cells, implanted, and serve as a transitional construct which is absorbed leaving an entirely new living tissue heart valve in vivo. In the approach, the tissue engineered heart valve can be seeded and immediately implanted, or seeded and cultured in a bioreactor before implantation. In the latter instance tissue formation and polymer bioabsorption can be complete before implantation or preferably continue after implantation. The advantages of developing tissue engineered heart valves would be several fold. First, the ultimate product would be a durable living heart valve able to withstand the demands of the body. It can be derived from non-immunogenic tissue obviating the need for anticoagulant therapy, furthermore, the tissue can be derived from an autologous source virtually eliminating the risk of disease transmission. In the case of infants and children where growth is a concern, the use of a living tissue valve would remove the need to replace the valve as the patient grows. Finally, in cases where repair rather than replacement is preferable, the tissue engineering solution would potentially provide a source of suitable living tissue.

Tissue engineered heart valves, and components of heart valves such as leaflets or supports, derived from polyhydroxyalkanoate polymers, which offer the necessary mechanical properties and bioabsorption profiles, may be produced by constructing porous heart valve scaffolds from these polymers alone or with other materials. Preferably, these scaffolds are derived from foams and/or fibrous polyhydroxyalkanaote polymers. The scaffolds, if desired, may be coated with other agents such as proteins to facilitate cell attachment and proliferation. The scaffolds are then subsequently seeded with the appropriate cells. Suitable cells include cardiovascular and vascular cells, smooth muscle cells, endothelial cells, as well as stem cells. Ideally, the cells are autologous but other non-immunogenic options are also acceptable. The seeded construct may then be incubated in a bioreactor prior to implantation. Preferably, the bioreactor subjects the heart valve to changes in flow and pressure, essentially mimicking in vivo conditions. A pulsatile bioreactor is preferred. At any time after seeding, the seeded construct may be implanted in vivo. Preferably, this is one to two weeks after seeding. Methods illustrative of the approach are described by Breuer, et al. Biotechnology & Bioengineering, 50:562–67 (1996); Shinoka, et al., *Ann. Thorac. Surg.* 60:S513–6, (1995); Zund et al., Euro. J. Cardio-thoracic Surgery 11:493–97 (1997).

Vascular Grafts

Vascular grafts are currently inserted to repair or replace compromised blood vessels, in the arterial or venous systems, that have been subject to damage or disease such as atherosclerosis, aneurysmal disease, and traumatic injury. Currently, there are three grafting options, namely, an autograft, a synthetic graft, or a cryopreserved graft when an autograft is not available. The choice between an autograft and a synthetic graft depends upon a number of factors. In general, synthetic grafts are restricted to applications involving the replacement of large and medium size vessels. Typically, these synthetic vessels remain open to blood flow for around 5 years before they begin to fail. Smaller diameter synthetic grafts, however, where blood flow rates are lower, generally fail rapidly, and thus are not used in procedures such as coronary artery bypass grafting (CABG), the most common open heart surgical procedure requiring smaller diameter vessels. When synthetic vascular grafts cannot be used (as in CABG),the preferred procedure involves the use of an autograft, which entails a second traumatic surgical procedure to harvest a suitable artery or vein from the patient. In some cases, the harvested vessels can be unsuitable for use, and in other cases there can be a shortage of harvestable autografts particularly if the patient has previously had the same operation. [It has been estimated that 40% of CABG patients receiving saphenous vein bypasses will require subsequent intervention within ten years of the original operation (Vector Securities International, Thoratec Laboratories Company Report, November 1997)]. For these reasons, there is a strong need to develop a vascular graft particularly for CABG procedures, and below the knee grafting procedures, which will remain open to blood flow, as well as larger diameter grafts to improve patency rates. Tissue engineered vascular graft, comprising cell seeded vascular scaffolds, which can be derived from polyhydroxyalkanoate polymers, offer such a solution to these problems. These polymers offer a suitable combination, either alone or with other materials, of bioabsorption rates and mechanical properties. Tissue engineered polyhydroxyalkanoate derived vascular grafts can be produced by forming a tubular construct of the appropriate diameter (typically 3–10 mm internal diameter) and seeding this construct with appropriate cells. Ideally, the polyhydroxyalkanoate is porous in nature, and the construct can be laminated. (In a variation of this approach, a non-cylindrical construct may be seeded and subsequently formed into a tubular construct.) The seeded tubular construct can be implanted directly, or preferably incubated in a bioreactor prior to implantation. Preferably, the bioreactor is capable of subjecting the construct to conditions similar to those experience in vivo, namely pulsatile flow. The cells are ideally autologous, and/or non-immunogenic. Suitable cells include cardiovascular cells, vascular cells, endothelial cells, smooth muscle cells, as well as stem cells. Methods illustrative of the approach are described by Shinoka, J. Thoracic & Cardiovascular Surgery, 115:536–546, Niklason, Science, 284:489–493 (1999).

IV. Methods of Fabricating the Devices

Preferred methods of fabricating medical devices include solvent casting, melt processing, extrusion, injection and compression molding, fiber firming, and spray drying. Particles are preferably prepared directly from a fermentation based process, or by a solvent evaporation technique, double emulsion technique, or by microfluidization, using methods available in the art. (Koosha, Ph.D. Dissertation, 1989, Univ. Nottingham, UK., *Diss. Abstr. Int. B* 51:1206 (1990); Bruhn & Müeller, *Proceed. Intern. Symp. Control. Rel. Bioact. Mater.* 18:668–69 (1991); Conti, et al., *J. Microencapsulation,* 9:153–66 (1992); Ogawa, et al., *Chem. Pharm. Bull.,* 36:1095–103 (1988); Mathiowitz & Langer, "Polyanhydride microspheres as drug delivery systems," in *Microcapsules Nanopart. Med. Pharm.* (Donbrow, Ed.) ch. 5, pp. 99–123 (CRC, Boca Raton, Fla. 1992)).

The PHAs can be fabricated into devices suitable for wound healing. For example, non-woven fibrous materials for this purpose may be prepared from the polymers by first producing polymer fibers, by pressing the polymers through a perforated outlet, using procedures known to those skilled in the art. The fibers can then be fabricated into a porous membrane (cloth) by spreading them on a solid support and subjecting them to compression molding. The thickness of the device is preferably less than 500 $\mu$m. The wound healing device may also be prepared by perforating a film or membrane using a laser to achieve porosity, or using a leaching technique to prepare a porous material. The pore sizes should ideally be small enough to lock out cells and other tissue matter. The wound healing devices may be positioned in vivo to separate tissues and stimulate tissue regeneration.

The PHAs may be used to encapsulate cells. Using procedures known to those skilled in the art, cells first may be pre-coated (see Maysinger, *Reviews in the Neurosciences,* 6:15–33(1995)). Using a particle encapsulation procedure such as the double emulsion technique, the cells may then be encapsulated by PHAs. Ogawa, et al., *Chem. Pharm. Bull.,* 36:1095–103 (1988). Encapsulated cells may then be implanted in vivo.

The PHAs may be fabricated into tissue engineering scaffolds using a wide range of polymer processing techniques. Preferred methods of fabricating PHA tissue engineering scaffolds include solvent casting, melt processing, fiber processing/spinning/weaving, or other means of fiber forming extrusion, injection and compression molding, lamination, and solvent leaching/solvent casting. Such methods are known to those skilled in the art.

One preferred method of fabricating a PHA tissue engineering scaffold involves using an extruder, such as a Brabender extruder. For example, this technique can be used to prepare extruded tubes suitable for implantation in a range of lengths and sizes.

Another preferred method involves preparing a nonwoven PHA scaffold from fibers. Fibers may be produced from the melt or solution, and processed into nonwovens using methods known to those skilled in the art. The properties of the nonwoven may be tailored by varying, for example, the PHA material, the fiber dimensions, fiber density, material thickness, fiber orientation, and method of fiber processing. The porous membranes may, if desired, be further processed. For example, these membranes may be formed into hollow tubes.

Another preferred method involves melt or solvent processing a suitable PHA into an appropriate mold and perforating the material using a laser or other means to achieve the desired porosity. Also preferred are methods that include rolling a compression molded PHA sheet into a loop and heat sealing. The PHA sheet optionally may be rolled with another material, such as a second biodegradable polymer. For example, the latter material can be a nonwoven of polyglycolic acid, polylactic acid, or a copolymer of glycolic and lactic acids, providing, for example, a laminated tube suitable for use in the engineering of new vessels, ducts, and tubes. The PHAs may also be used to coat other tissue engineering scaffolds. Such materials could be derived from other degradable polymers. Coating may be performed, for example, with a solvent based solution, or by melt techniques, or using a PHA latex.

The tissue engineering devices described herein may be seeded with cells prior to implantation or after implantation. The cells may be harvested from a healthy section of the donor's tissue, expanded in vitro using cell culture techniques, and then seeded into a scaffold (or matrix) either prior to or after implantation. Alternatively, the cells may be obtained from other donor's tissue or from existing cell lines.

The PHAs may be used to coat other devices and materials. Such coatings may improve their properties for medical application, for example, improving their biocompatibility, mechanical properties, and tailoring their degradation and controlled release profiles. The PHAs may be coated onto other devices using the fabrication procedures described above. The thickness of the coating can be adjusted to the needs of the specific application by changing the coating weight or concentration applied, and/or by overcoating.

The PHAs may be fabricated into stents using a wide range of polymer processing techniques. Preferred methods of fabricating PHA stents include solvent casting, melt processing, fiber processing/spinning, extrusion, laser ablation, injection molding, and compression molding. Such methods are known to those skilled in the art.

Methods for manufacturing the devices which increase porosity or exposed surface area can be used to alter degradability. For example, as demonstrated by the examples, porous polyhydroxyalkanoates can be made using methods that creates pores, voids, or interstitial spacing, such as an emulsion or spray drying technique, or which incorporate leachable or lyophilizable particles within the polymer.

Additional methods for fabricating the polyhydroxyalkanoate devices are described in Biomaterials Science (Ratner, et al., Eds.) Academic Press, San Diego, Calif. 1996; Biomedical Applications of Polymeric Materials (Tsuruta, et al., Eds.) CRC Press, Boca Raton, Fla., 1993; Synthetic Biodegradable Polymer Scaffolds (Atala, et al., Eds.) Birhauser, Boston, 1997; Wound Closure Biomaterials and Devices, (Chu, Jet al., Eds.) CRC Press, Boca Raton, Fla., 1997; Polyurethanes in Biomedical Applications (Lamba, et al., Eds.) CRC Press, Boca Raton, Fla., 1998; Handbook of Biodegradable Polymers (Domb, et al., Eds.) Harwood Academic Publishers, Amsterdam, The Netherlands, 1997.

V. Using the Devices and Composition

The polyhydroxyalkanoate devices (including coatings) and composition, can be delivered by any means including open surgery or by a minimally invasive method such as ingestion or injection or insertion. Furthermore, depending upon the application, the composition may be further modified to include other materials, such as bioactive agents like growth factors, drugs, antimicrobial agents, angiogenesis factors, or materials that modify the properties of the device such as other polymers, plasticizers, nucleants, and fillers.

When the depyrogenated PHAs are implanted in the body, these materials show very little, if any, acute inflammatory reaction or any adverse tissue reaction. There is no significant inflammatory response or scar tissue formation. Recruitment of inflammatory cells is minimal. Histological examination of the explanted devices demonstrates that the materials are essentially inert. Accordingly, devices constructed of PHAs can be implanted with minimal adverse affect on the surrounding tissue. Release of the hydroxy acid degradation products from the implanted materials typically is slow and well tolerated by the body. Thus, PHAs are expected to maintain their material properties for a matter of months and will eventually degrade to non-toxic materials.

Devices prepared from the PHAs can be used for a wide range of different medical applications. Examples of such applications include controlled release, drug delivery, tissue engineering scaffolds, cell encapsulation, targeted delivery, biocompatible coatings, biocompatible implants, guided tissue regeneration, wound dressings, orthopedic devices, prosthetics and bone cements (including adhesives and/or structural fillers), and diagnostics.

The PHAs can encapsulate, be mixed with, or be ionically or covalently coupled to any of a variety of therapeutic, prophylactic or diagnostic agents. A wide variety of biologically active materials can be encapsulated or incorporated, either for delivery to a site by the polyhydroxyalkanoate, or to impart properties to the polymer, such as bioadhesion, cell attachment, enhancement of cell growth, inhibition of bacterial growth, and prevention of clot formation.

Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Compounds with a wide range of molecular weight can be encapsulated, for example, between 100 and 500,000 grams or more per mole. Examples of suitable materials include proteins such as antibodies, receptor ligands, and enzymes, peptides such as adhesion peptides, saccharides and polysaccharides, synthetic organic or inorganic drugs, and nucleic acids. Examples of materials which can be encapsulated include enzymes, blood clotting factors, inhibitors or clot dissolving agents such as streptokinase and tissue plasminogen activator; antigens for immunization; hormones and growth factors; polysaccharides such as heparin; oligonucleotides such as antisense oligonucleotides and ribozymes and retroviral vectors for use in gene therapy. The polymer can also be used to encapsulate cells and tissues. Representative diagnostic agents are agents detectable by x-ray, fluorescence, magnetic resonance imaging, radioactivity, ultrasound, computer tomography (CT) and positron emission tomography (PET). Ultrasound diagnostic agents are typically a gas such as air, oxygen or perfluorocarbons.

In the case of controlled release, a wide range of different bioactive compounds can be incorporated into a controlled release device. These include hydrophobic, hydrophilic, and high molecular weight macromolecules such as proteins. The bioactive compound can be incorporated into the PHAs in a percent loading of between 0.1% and 70% by weight, more preferably between 5% and 50% by weight. The PHAs may be in almost any physical form, such as a powder, film, molded item, particles, spheres, latexes, and crystalline or amorphous materials. They can be combined with additional non-PHA materials, for example, other polymers. They are suitable for use in applications requiring slowly degrading, biocompatible, moldable materials, for example, medical devices. Examples of medical devices which can be prepared from the polymers include rods, bone screws, pins, surgical sutures, stents, tissue engineering devices, drug delivery devices, wound dressings, and patches such as hernial patches and pericardial patches.

Degradable implants fabricated with the PHAs may be used in a wide range of orthopedic and vascular applications, tissue engineering, guided tissue regeneration, and applications currently served by other thermoplastic elastomers (McMillin, *Rubber Chem. Technol.*, 67:417–46 (1994)). The implants may include other factors to stimulate repair and healing. Preferred devices are tubes suitable for passage of bodily fluids. These devices may be modified with cell attachment factors, growth factors, peptides, and antibodies and their fragments.

Prior to implantation, a bioresorbable polymeric article must be sterilized to prevent disease and infection of the recipient. Sterilization is performed prior to seeding a polymeric device with cells. Heat sterilization of PHA containing articles is often impractical since the heat treatment could deform the article, especially if the PHA has a melting temperature below that required for the heat sterilization treatment. This problem can be overcome using cold ethylene oxide gas as a sterilizing agent. Exposure of a PHA containing article to vapors of ethylene oxide prior to implantation sterilizes the article making it suitable for implantation. During sterilization with cold ethylene oxide gas, gamma-irradiation, the PHA containing article maintains its shape. This type of treatment is ideally suited for sterilization of molded, or pre-formed articles where the shape of the article plays in important role in its proper functioning.

The devices described herein can be administered systemically or locally, or even used in vitro, particularly for cell culture. The preferred methods of systemically administering the devices are by injection, inhalation, oral administration and implantation. Other suitable methods for administering the devices include administering the devices topically, as a lotion, ointment, patch, or dressing.

The compositions and methods described herein will be further understood with reference to the following non-limiting examples.

EXAMPLE 1

Production of P4HB in Recombinant *E. coli*

*E. coli* strain MBX1177, a derivative of strain DH5α selected for the ability to grow with 4-hydroxybutyric acid (4HB) as the sole carbon source, was transformed with pFS30, a plasmid containing the genes encoding PHA synthase from *Ralstonia eutropha*, 4-hydroxybutyryl-CoA transferase from *Clostridium kluyveri*, and β-lactamase, which confers resistance to ampicillin. The synthase and transferase are under the control of the trc promoter, which is inducible by isopropyl-β-D-thiogalactopyranoside (IPTG) in pFS30. These cells were first grown in 100 ml LB (Luria Broth, Difco, Detroit, Mich.; 25 g/L) plus 100 μg/ml ampicillin overnight in a 250-ml Erlenmeyer flask at 37° C. with shaking at 200 rpm. This entire culture was used as an inoculum for the fermentation carried out in a 7 L vessel. The first stage of the fermentation consisted of growing biomass in 5 L of LB-ampicillin at 37° C. with stirring at 800 rpm and aeration at 1 volumetric volume of air/min (vvm). After 17 hours, the volume was adjusted to 6 L by adding one liter of medium, such that the total volume contained, per liter: 2.5 g LB powder, 5 g 4HB as sodium salt, 2 g glucose, 50 mmol potassium phosphate (pH 7), 7 g phosphoric acid, 100 μg ampicillin, and 0.1 mmol IPTG. At this time, the temperature was adjusted to 33° C., and the agitation rate was reduced to 400 rpm. Periodic additions of glucose and sodium 4HB were made when the pH was significantly below or above 7, respectively, because the addition of glucose caused the pH to decrease slowly and the addition of 4HB caused the pH to increase slowly. The pH was not automatically controlled. The fermentation proceeded this way for an additional 70 h, at which time a total of 34 g/L glucose and 15 g/L 4HB had been fed. The cells were allowed to settle at 4° C. for 2 days, after which time the liquid phase was pumped away, and the cell slurry was fluidized in a Microfluidics Corporation (Newton, Mass.) M110-EH Microfluidizer at 18,000 psi. The resulting material was lyophilized and extracted into tetrahydrofuran (THF, 3% wt/vol P4HB) with heating (60° C.) and mechanical stirring. The resulting THF extract was pressure filtered through glass micro-fiber (2.3 μm) and Teflon (2 μm) depth filters. The polymer was precipitated into an equal volume of water and lyophilized. The polymer was redissolved in THF (3% wt/vol P4HB) with heating (60° C.) and the solution was filtered through glass micro-fiber (2.3 μm) and Teflon (2 μm) depth filters and precipitated into water/THF (1:1). The precipitate was washed with water/THF (1:1) and lyophilize to yield a white colored foam (20 g). This material was identified as poly-4-hydroxybutyrate and shown to be non-cytotoxic by an agar diffusion assay (ISO 10993, Toxicon Corp., Bedford, Mass.). Elemental analysis was C, 55.63%; H, 7.41%; O, 37.28%; N, 41 ppm. GC analysis shows very low lipids in the purified polymer. NMR analysis shows expected peaks and no lipids.

EXAMPLE 2

Production of Poly(4HB-co-2HB) in Recombinant *E. coli*

*E. coli* strains MBX1177/pFS30 and MBX184 (CGSC6966)/pFS30 were precultured in 300 mL LB-ampicillin in a one-liter Erlenmeyer flask at 30° C. overnight with shaking at 200 rpm. Two 100-mL aliquots of each preculture were centrifuged (2000×g, 10 minutes), and the cells obtained from each of these aliquots were resuspended in 100 mL of a medium containing, per liter: 6.25 g LB powder; 2 g glucose; 50 mmol potassium phosphate (pH 7); 100 μg ampicillin; and 100 μmol IPTG. The medium also contained 2-hydroxybutyric acid (2HB) and 4HB; in one flask the concentrations were 8 g/L 2HB and 2 g/L 4HB, and in the other the concentrations of the two acids were each 5 g/L. Both acids were added to the flasks as the sodium salt; the masses given for the acids do not include the mass of sodium. These four flasks (two flasks for each strain) were incubated at 30° C. for an additional 48 hours with shaking at 200 rpm. The cells were removed from the medium by centrifugation (2000×g, 10 minutes), washed once with water, centrifuged again, and lyophilized. Gas chromatographic analysis was carried out on the lyophilized cell mass to analyze for polymer content and composition. The cellular contents and compositions of the PHAs produced are shown in Table 2. When the ratio of 2HB to 4HB was 4:1, the 2HB content of the polymer was higher than 19 percent for both strains by GC analysis, while at a 1:1 ratio of 2HB to 4HB, the 2HB content of the polymer was around 1 percent. The 4HB was more readily incorporated into the polymer than was the 2HB; therefore, when 4HB was present at 2 g/L the overall polymer content of the cells is less than when it was present at 5 g/L. The polymers produced by MBX184/pFS30 were extracted from the cells and analyzed. The lyophilized cell mass was incubated in 5 mL of chloroform at 37° C. for 2 hours. The cell debris was removed by centrifugation (2000×g, 5 minutes), and the resulting polymer solution was added dropwise to 50 mL of ethanol to precipitate it. The precipitated polymer was centrifuged from the ethanol as described above. In the case of the 4:1 2HB:4HB ratio, the polymer was difficult to centrifuge from the ethanol; it formed a haze when added to the ethanol, but not nearly all of it could be collected by centrifugation, probably because the molecular weight of this polymer was rather low. The polymer isolated from the 1:1 2HB:4HB flask was easily precipitated from the ethanol, and it was recovered nearly completely. GC analysis of these extracted samples (Table 2) show that the 2HB content was slightly lower than when the analysis was done on whole cells. It is possible that 2HB residues in the polymer chain are hydrolyzed during the extraction, thus lowering the apparent 2HB content in the extracted samples. The fact that the molecular weight of the extracted polymer was apparently lower when the 2HB content was higher is consistent with this explanation.

A second experiment was performed with MBX184/pFS30. These cells were precultured in 400 mL LB-ampicillin in a one-liter Erlenmeyer flask at 30° C. overnight with shaking at 200 rpm. An addition of 20 ml of medium was made to each flask such that the total volume contained, per liter: 2.5 g additional LB powder; 2 g 4HB as sodium salt; 2 g glucose; 50 mmol potassium phosphate (pH 7); 100 μg ampicillin; 50 μmol IPTG; and 2, 4, 6, or 8 g 2HB as sodium salt. The flasks were incubated for an additional 48 hours at 30° C. and 200 rpm. The cells were removed from the medium by centrifugation (2000×g, 10 minutes), washed once with water, centrifuged again, and lyophilized. The dried cell mass was subjected to GC analysis as described above. Table 3 shows the cell content and composition of the polymers thus obtained. At low 2HB:4HB ratios, little or no 2HB was incorporated into the polymer; however, when this ratio was 3:1 or 4:1, 2HB incorporation into the polymer was very significant. The overall polymer content of all the cells was rather low, probably because the acids are not present at concentrations high enough to permit the uptake and/or incorporation to proceed at a high rate.

TABLE 2

GC Analysis of Poly(4HB-co-2HB)
From MBX1177/pFS30 and MBX184/pFS30

| Strain | 4HB, g/L | 2HB, g/L | Total PHA, % of dcw[a] | P4HB, % of PHA[b] | P2HB, % of PHA[b] |
|---|---|---|---|---|---|
| 184/30 | 2 | 8 | 18.3 | 70.8 | 19.2(14.2)[c] |
| 184/30 | 5 | 5 | 47.1 | 98.8 | 1.2(0.9)[c] |
| 1177/30 | 2 | 8 | 13.0 | 62.3 | 27.7 |
| 1177/30 | 5 | 5 | 40.1 | 98.9 | 1.1 |

[a]dcw: dry cell weight.
[b]Determined by GC analysis. About 20 mg of lyophilized cell mass was subjected to butanolysis at 110° C. for 3 hours in 2 mL of a mixture containing (by volume) 90% 1-butanol and 10% concentrated hydrochloric acid, with 2 mg/mL benzoic acid added as an internal standard. The water-soluble components of the resulting mixture were removed by extraction with 3 mL water. The organic phase (1 μL at a split ratio of 1:50 at an overall flow rate of 2 mL/min) was analyzed on an SPB-1 fused silica capillary GC column (30 m; 0.32 mm ID; 0.25 μm film; Supelco; Bellefonte, Pa.) with the following temperature profile: 80° C., 2 min.; 10° C. per min. to 250° C.; 250° C., 2 min. The standard used to test for the presence of 4-hydroxybutyrate units in the polymer was γ-butyrolactone. The standard used to test for 2-hydroxybutyrate units in the polymer was sodium (2-hydroxybutyrate).
[c]Percentages in parentheses were determined by GC analysis as above, but after extraction of the polymer into chloroform and subsequent precipitation in ethanol.

TABLE 3

GC Analysis of Poly(4HB-co-2HB) From MBX184/pFS30

| Sample | 4HB, g/L | 2HB, g/L | Total PHA, % of dcw[a] | P4HB, % of PHA[b] | P2HB, % of PHA[b] |
|---|---|---|---|---|---|
| 1 | 2 | 2 | 8.2 | 100 | 0 |
| 2 | 2 | 4 | 5.6 | 100 | 0 |
| 3 | 2 | 6 | 5.7 | 84.1 | 15.9 |
| 4 | 2 | 8 | 4.1 | 54.3 | 45.7 |

[a]dcw: dry cell weight.
[b]Determined by GC analysis. See Table 2 for details.

EXAMPLE 3

Production of poly(4HB-co-3HB) in Recombinant *E. coli*

Strain MBX1177/pFS30 was precultured in 100 ml LB-ampicillin in four separate 250-ml Erlenmeyer flasks at 30° C. overnight with shaking at 200 rpm. An addition of 20 ml of medium was made to each flask such that the total volume contained, per liter: 2.5 g additional LB powder; 4 g 4HB as sodium salt; 4 g glucose; 50 mmol potassium phosphate (pH 7); 100 μg ampicillin; 50 μmol IPTG; and 0.25, 0.5, 0.75, or 1 g 3-hydroxybutyrate (3HB) as sodium salt. The flasks were incubated for an additional 48 hours at 30° C. and 200 rpm. The cells were removed from the medium by centrifugation (2000×g, 10 minutes), washed once with water, centrifuged again, and lyophilized. Gas chromatographic analysis was carried out on the lyophilized cell mass to analyze for polymer content and composition. The standard used to test for 3-hydroxybutyrate units in the polymer was poly(3-hydroxybutyrate). The cellular contents and compositions of the PHAs produced are given in Table 4. As the ratio of 4HB/3HB in the medium decreased, the 3HB content of the polymer increased in a monotonic fashion, while the overall polymer content of the cells was similar in all trials, which means that the composition of the medium can be used predictably to control the copolymer composition without significantly affecting the overall polymer yield. The polymer was extracted from the remainder of the lyophilized cell mass. For all samples, lyophilized cell mass was mixed with about three times its own volume of 1,2-dichloroethane and incubated with mild shaking in a closed tube at 37° C. for 6 hours. The particulate matter was separated from the polymer solution by centrifugation (2000×g, 10 minutes). The resulting solution was added dropwise to about 10 times its own volume of ethanol, and the precipitated polymer was allowed to settle out of solution. The supernatant was poured off, and the remaining wet polymer was allowed to stand until it appeared to be dry. The polymer was then lyophilized to complete dryness. Thermal properties of these P4HB-co-3HB compositions are shown in Table 5.

TABLE 4

GC Analysis of Poly(4HB-co-3HB) From MBX1177/pFS30

| Sample | 4HB, g/L | 3HB, g/L | Total PHA, % of dcw[a] | P4HB, % of PHA[b] | P3HB, % of PHA[b] |
|---|---|---|---|---|---|
| 3a | 4 | 0.25 | 49.3 | 98.0 | 2.0 |
| 3b | 4 | 0.5 | 46.7 | 94.2 | 5.8 |
| 3c | 4 | 0.75 | 56.6 | 91.7 | 8.3 |
| 3d | 4 | 1 | 51.8 | 89.4 | 10.6 |

[a]dcw: dry cell weight.
[b]Determined by GC analysis. See Table 2 for details. The standard used to test for the presence of 4-hydroxybutyrate units in the polymer was γ-butyrolactone. The standard used to test for 3-hydroxybutyrate units in the polymer was poly(3-hydroxybutyrate).

TABLE 5

Properties of P4HB and P4HB-co-3HB From MBX1177/pFS30

| Sample | %[a] 4HB | %[a] 3HB | Tm[b] (° C.) | dH Tm1[b] (J/g) | Tg[b] (° C.) | Tx[b] (° C.) | Tm2[b] (° C.) | Mw[c] |
|---|---|---|---|---|---|---|---|---|
| P4HB | 100 | 0 | 60 | 45 | −51 | −16 | X | 1,000,000 |
| 3b | 94.2 | 5.8 | 47 | 36 | −52 | −4 | 44 | 1,500,000 |
| 3c | 91.7 | 8.3 | 40 | 20 | −53 | nd | 39 | 1,900,000 |
| 3d | 89.4 | 10.6 | 39 | 17 | −53 | nd | nd | 1,100,000 | nd = not detected.
[a]Determined by GC analysis, see Table 2 for details.
[b]Determined by DSC analysis. A Perkin Elmer Pyris 1 differential scanning calorimeter was used. Samples masses were approximately 4–8 mg. The thermal program used was as follows: 25° C., 2 min.; heat to 195° C. at 10° C. per min.; hold at 195° C. 2 min.; cool to −80° C. at 300° C. per min.; hold at −80° C. for 2 min.; heat to 195° C. at 10° C. per min. The melting temperature (Tm) and the enthalpy of fusion of this melting peak (dHTm1) were determined in the first heating cycle. Glass transition temperature (Tg), crystallization temperature (Tx) and melting temperature (Tm2) were determined during the second heating cycle.
[c]Determined by GPC analysis. Isolated polymers were dissolved in chloroform at approximately 1 mg/mL and samples (50 μL) were chromatographed on a Waters Stryagel HT6E column at a flow rate of 1 mL chloroform per minute at room temperature using a refractive index detector. Weight Average molecular weights of the polymers were determined relative to polystyrene standards of narrow polydispersity.

EXAMPLE 4

In Vitro and In Vivo Degradation of P4HB

The degradation of P4HB was studied in vitro and in vivo. Three different configurations of varying porosity (0%, 50% and 80% porosity) were examined. Small disks (5 mm diameter) were punched from compression molded P4HB films of uniform thickness. Porous samples of P4HB were produced using the salt leaching technique described below. The degradation behavior in vitro was studied by incubating the disks in a sterile, phosphate buffer (8 mM sodium phosphate, 2 mM potassium phosphate, 140 mM NaCl, 10 mM KCl, pH 7.4, containing NaN$_3$ as preservative) at 37° C. The degradation behavior in vivo was studied after implantation in subcutaneous pockets in rats.

Preparation of Porous P4HB

Classified sodium chloride crystals (80–180 μm) were mixed with molten P4HB. (Note that the polymer salt ratio can be adjusted to produce the desired porosity, while particle size may be adjusted to produce pores of varying size.) The polymer salt mixture was pressed into a thin film. After allowing the material to solidify, the film was removed from the mylar backing. The film was exhaustively extracted with water to remove the salt, leaving a porous film of P4HB.

Accelerated Degradation of P4HB

Figure 3:
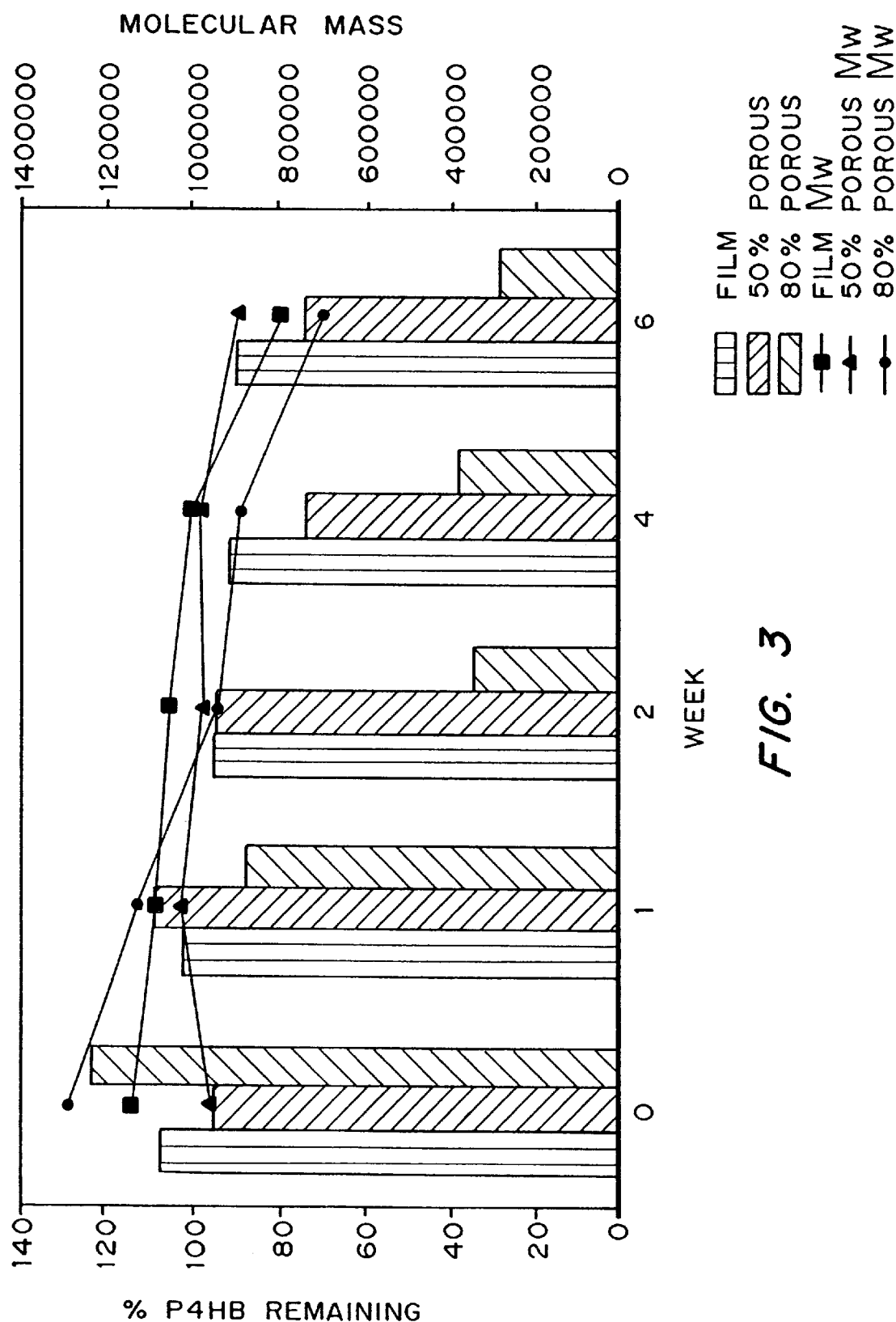
FIG. 3 is a graph of P4HB degradation in vivo over time (weeks).

The degradation of P4HB was studied in vivo. Three different configurations of varying porosity (0%, 50%, and 80% porosity) were examined. Small disks (5 mm diam.) were punched from compression molded P4HB films of uniform thickness. Porous samples of P4HB were produced using a salt leaching technique. The degradation behavior in vivo was studied after implantation in subcutaneous pockets in rats. Samples were removed at various times. The molecular mass was measured by GPC and mass loss was measured by quantification of the remaining 4HB by CG analysis. The results are shown in FIG. 3. As shown in FIG. 3, the sample mass loss varied with porosity. Film, 50%, and 80% porous samples showed a 5%, 20%, and 75% mass loss, respectively, over the six week period, while the average molecular mass loss of these samples also decreased significantly (20 to 50%). These data demonstrate that the degradation rate of PHAs can be modified and controlled by altering porosity and increasing surface area.

Results

The P4HB implants showed a very minimal inflammatory response, much less so than for a PGA non-woven mesh. This is a very good indication of the biocompatibility of these materials. Samples were removed at various times and evaluated histologically both as to the implants and surrounding tissue. The molecular mass was measured by GPC and mass loss was measured by quantification of the remaining 4HB by GC analysis. The results are shown in Tables 6 and 7. As shown in Table 6, P4HB does not degrade significantly over a ten week period in vitro. All of the samples maintained their starting weight, and there was about a 20 to 40% decrease in average molecular mass. The samples incubated in vivo showed much more pronounced degradation. The mass loss varied with porosity. Film, 50%, and 80% porous samples showed a 20%, 50%, and 100% mass loss, respectively, over the ten week period, while the average molecular mass loss of these samples also decreased significantly (20 to 50%).

Light microscopic and environmental scanning electron microscopy (ESEM) examination of the samples show almost no discernible change for the in vitro samples over the ten week incubation period. In contrast, the in vivo implants show distinct signs of degradation. The surface of these materials became progressively degraded during the ten week implantation period. After one week, the film samples showed some signs of cracking and crazing, which progressed to surface erosion and pitting over the following nine weeks.

The in vitro degradation data suggest that P4HB is fairly stable to simple hydrolysis, unlike other polyesters used in bioresorbable applications, such as PGA, PLA and their copolymers. However, the degradation of the implants indicated that P4HB can be degraded in vivo, suggesting a biologically mediated mode of degradation. The data shows increasing degradation with increasing porosity, which indicates that surface area of the polymer implant plays a role in its degradation in vivo. This suggests that the degradation of P4HB polymers in vivo occurs at the surface of the implant, unlike PGA or PLA materials which degrade throughout the implant by hydrolysis, with associated molecular mass decrease and loss of mechanical properties. These data suggest that the degradation rate of P4HB can be modified and controlled by altering its surface area. Also, it is expected that this type of surface degradation will result in a relatively slow rate of molecular mass loss allowing for the maintenance of polymer material properties longer than existing absorbable, medical polyesters. The P4HB implants were very well tolerated and showed only a very minimal foreign body reaction. These findings show that these materials have significant advantages over existing biomedical polyesters.

TABLE 6

Degradation of P4HB In Vitro:
Percent Original Mass Remaining and Molecular Mass

| Implantation (weeks) | Film Wt % Remain.[a] | Film Molec. Mass[b] | 50% Por. Wt % Remain.[a] | 50% Por. Molec. Mass[b] | 80% Por. Wt % Remain.[a] | 80% Por. Molec. Mass[b] |
|---|---|---|---|---|---|---|
| 0 | 108 | 1144592 | 96 | 963145 | 123 | 1291117 |
| 1 | 97 | 1160707 | 93 | 1103860 | 99 | 968245 |
| 2 | 101 | 1008496 | 98 | 1055614 | 106 | 1072328 |
| 4 | 100 | 887005 | 96 | 725089 | 116 | 987665 |
| 6 | 109 | 896521 | 97 | 764260 | 95 | 1049079 |
| 10 | 92 | 772485 | 90 | 605608 | 100 | 727543 |

[a]Determined by GPC analysis. See Table 3 for details.
[b]Determined by quantitative GC analysis. See Table 2 for details.

TABLE 7

Degradation of P4HB In Vivo:
Percent Original Mass Remaining and Molecular Mass

| Implantation (weeks) | Film Wt % Remain.[a] | Film Molec. Mass[b] | 50% Por. Wt % Remain.[a] | 50% Por. Molec. Mass[b] | 80% Por. Wt % Remain.[a] | 80% Por. Molec. Mass[b] |
|---|---|---|---|---|---|---|
| 0 | 108 | 1144592 | 96 | 963145 | 123 | 1291117 |
| 1 | 103 | 1091107 | 109 | 1026821 | 88 | 1132492 |
| 2 | 95 | 1054873 | 94 | 973830 | 35 | 943960 |
| 4 | 92 | 1007736 | 73 | 989629 | 39 | 881919 |
| 6 | 90 | 797170 | 74 | 901330 | 28 | 689157 |
| 10 | 80 | 716296 | 48 | 647175 | 0 | nd |

[a]Determined by GPC analysis. See Table 3 for details.
[b]Determined by GC analysis. See Table 2 for details. Explants often weighed more than the original implant due to the presence of adherent tissue or coagulated blood. Therefore, the mass of P4HB in the explant was determined by quantitative GC analysis. Weight percent remaining P4HB was taken as this mass divided by original implant.

EXAMPLE 5

Compression Molding

P4HB was pressed into a thin film using Carver hydraulic press. The platens were heated to 115° C. P4HB was pressed between two sheets of mylar using metal spacers. Spacer thickness and pressure of the press were adjusted to control film thickness. The film was removed from the press and allowed to cool to room temperature. After solidifying (within a matter of seconds), the this was easily peeled from the mylar backing material. Mechanical data for this material is shown in Table 1. The rapid solidification of P4HB demonstrates its rapid crystallization.

TABLE 1

Thermal and Mechanical Properties of Selected Medical Polymers

| Polymer | Tm (° C.) | Tg (° C.) | Tensile Str. (psi) | Modulus (psi) | Elongation (%) | Degradation |
|---|---|---|---|---|---|---|
| [1]P4HB | 60 | −51 | 7,500 | 9,400 | 1000 | depends on config. |

TABLE 1-continued

Thermal and Mechanical Properties of Selected Medical Polymers

| Polymer | Tm (° C.) | Tg (° C.) | Tensile Str. (psi) | Modulus (psi) | Elongation (%) | Degradation |
|---|---|---|---|---|---|---|
| [1]pP4HB50[a] | 60 | −51 | 895 | 2155 | 164 | depends on config. |
| [1]pP4HB80[b] | 60 | −51 | 180 | 257 | 100 | depends on config. |
| [6]P4HB-3HB 10% | 50 | −42 | 9,000 | 14,500 | 1080 | Not reported |
| [1]PHB | 175 | 0 | 4,000 | 110,000 | 4 | >52 wks |
| [2]PGA | 230 | 35 | 10,000 | 1,000,000 | 17 | 8 wks |
| [3]PDLLA | Am | 53 | 5,000 | 300,000 | 5 | <8 wks |
| [3]PLLA | 175 | 55 | 10,000 | 500,000 | 8 | >8 wks |
| [2]DLPLG 50/50 | Am | 48 | 7,000 | 300,000 | 5 | 3–8 wks |
| [5]LDPE | | | 2,000 | | 400–700 | Nondegradable |
| [5]HDPE | | | 4,000 | | 100–1000 | Nondegradable |
| [5]UHMWPE | | | 7,250 | | 450 | Nondegradable |
| PP | | | 4,000 | 20,000 | 200–700 | Nondegradable |
| PET | | | 8,500 | | 50 | Nondegradable |
| PTFE | | | 3,000 @ Yield | 50,000 | 300 | Nondegradable |

[a]pP4HB50, 50% porous P4HB, see example 7.
[b]pP4HB80, 80% porous P4HB, see example 7.
Table References:
[1]From this work measured according to ASTMD638 at ambient temperature and a strain rate of 0.05 or 0.1 in./min..
[2]Hutmacher et al. Int. J. Oral Max. Imp. 1996, 11: 667–78.
[3]Nobes et al. submitted.
[4]Mark, Physical Properties of Polymers Handbook, American Inst. of Physics, Woodbury, New York, 1996.
[5]Schwartz, S. S. and Goodman, S. H. Plastic Materials and Processes, Van Nostrand Reinhold Company, New York, 1982.
[6]Saito, Y. and Doi, Y. Int. J. Biol. Macromol. (1994) 16: 99–104.

EXAMPLE 6

Compression Molding of Porous P4HB

Classified sodium chloride crystals (80–180 μm) were mixed with molten P4HB as described in Examples 4 and 5. (The polymer salt ratio can be adjusted to produce the desired porosity, while particle size may be adjusted to produce pores of varying size.) The polymer salt mixture was pressed into a thin film using the conditions described in Example 6. After allowing the material to solidify, the film was removed from the mylar backing. The film was exhaustively extracted with water to remove the salt, leaving a porous film of P4HB. Salt removal was monitored by analysis of chloride in the supernatant and confirmed by elemental analysis of the leached film (less than 0.5% chloride). Mechanical data for 50% and 80% porous P4HB (pP4HB50 and pP4HB80, respectively) is shown in Table 1.

EXAMPLE 7

Cell Seeding of P4HB Scaffolds

Porous P4HB, as described in Example 6, was sterilized by cold ethylene oxide treatment. It was seeded with ovine vascular cells and cultured in vitro. Preliminary data indicated very good attachment of these cells to the material. This is a further demonstration of the biocompatibility of this material. The number of cells attached to the material can be quantified using an assay for DNA and compared with the standard for tissue engineering scaffolds, PGA mesh.

EXAMPLE 8

P4HB Fiber Orientation

Compression molded strips of P4HB were uniaxially stretched. The sample narrowed and became clear, showing signs of necking. After this stretching process, the polymer appeared stronger and somewhat more flexible, demonstrating uniaxial orientation of the sample.

EXAMPLE 9

Production of P4HB Foam

A thermal phase separation method was used to make P4HB foam. First, P4HB was dissolved in dioxane at 1 to 5% wt./vol. This polymer solution was cast as a thick film and solidified by cooling on ice below the melting point of dioxane. The solvent was evaporated from this solid material at low pressure to yield a porous foam with the approximate dimensions of the starting thick film. ESEM analysis of this material showed a highly porous, sponge-like structure. The polymer concentration and cooling process can be varied to alter the porosity of the foam. Prior to freezing, the polymer solution can be shaped into a variety of forms, broken up into particulate material or used as a coating. Therefore, this thermal phase separation technique can be used to produce a great variety of highly porous, 3-dimensional shapes of P4HB.

EXAMPLE 10

P4HB Coating of a PGA Non-Woven Mesh

P4HB was dissolved in tetrahydrofuran at 1% wt/vol. A 1 mm thick non-woven mesh of PGA (Albany International, bulk density 52 mg/cc) was dipped into this solution so that the air voids were eliminated. The coated mesh was allowed to air dry, and the coating procedure was repeated. Light microscopic and ESEM analyses of the coated mesh showed that during the drying process the polymer migrated to the fiber intersections, and functioned to bind the fibers together.

This fiber bonding technique was found to dramatically improve the strength and handleability of the PGA mesh. Tensile testing according to ASTM D638, showed that the tensile strength, Young's modulus, and ultimate elongation of this material were 130 psi, 240 psi, and 171%, respectively. This was a dramatic improvement over the uncoated material which was too fragile to test these parameters.

EXAMPLE 11

P4HB Foam Coating of a PGA Non-Woven Mesh

P4HB was dissolved in dioxane at 2.5% wt/vol. A 1 mm thick non-woven mesh of PGA (Albany International, bulk density 52 mg/cc) was dipped into this solution so that the air voids were eliminated. The coated mesh was cooled on ice so that the coating solution solidified. The mesh was freeze-dried to remove the dioxane. Light microscopic analysis of the coated mesh showed that during the freeze-drying process the polymer formed a web-like foam throughout the PGA mesh. This foamed material has good handleability. The high surface area and improved mechanical properties are attractive for a variety of applications.

EXAMPLE 12

Formation of P4HB Microspheres

P4HB was dissolved in dichloromethane at 1% wt/vol. A 1 ml volume of this solution was mixed with 5 ml of a 0.5% wt/vol. solution of sodium dodecylsufate (SDS). The two phase mixture was mechanically mixed to yield an emulsion. A stream of nitrogen was bubbled through the mixture for 1 hour with rapid stirring to facilitate removal of the dichloromethane. The mixture was stirred open to the air overnight to allow for the complete removal of dichloromethane. The resultant suspension contained P4HB microspheres of about 1–10 μm, as determined under a phase contrast optical microscope.

CONCLUSIONS FROM EXAMPLES

Polyhydroxyalkanoates such as the homopolymer P4HB and copolymers containing 4HB have physical properties and degradation characteristics which make them very attractive as implants for use in medical applications. These polymers can be fabricated into fibers, sheets, foams, coating, structures, filaments and the like for use of these as implantable medical materials.

Modifications and variations of the present invention will be obvious to those of skill in the art from the foregoing detailed description. Such modifications and variations are intended to come within the scope of the following claims.

We claim:

1. A biodegradable polyhydroxyalkanoate composition comprising a polyhydroxyalkanoate polymer having a controlled degradation rate of less than one year in vivo, under physiological conditions, wherein the degradation rate of the polyhydroxyalkanoate polymer is manipulated through addition of components to the polymeric composition, selection of the chemical composition of the polyhydroxyalkanoate polymer through selection of monomeric units, as chemical linkages, which are incorporated into the polymer, by alteration of the linkages, chemical backbone or pendant groups, molecular weight, processing conditions, or form of the composition, and wherein the polyhydroxyalkanoate polymer has a weight average molecular weight of between 10,000 and 10,000,000 Dalton; and wherein the form of the composition refers to the porousness and surface area of the composition.

2. The composition of claim 1 wherein the chemical composition of the polyhydroxyalkanoate is altered by alteration of the linkages, or chemical backbone or pendant groups.

3. The composition of claim 1 wherein the polyhydroxyalkanoate polymer is selected from the group of consisting of poly-4-hydroxybutyrate, poly-4-hydroxybutyrate-co-3-hydroxybutyrate, poly-4-hydroxybutyrate-co-2-hydroxybutyrate, and copolymers and blends thereof.

4. The composition of claim 1 wherein the polyhydroxyalkanoate polymer is selected from the group consisting of poly-3-hydroxybutyrate-co-3-hydroxyhexanoate, poly-3-hydroxybutyrate-co-3-hydroxyoctanoate, poly-3-hydroxybutryrate-co-3-hydroxydecanoate, and copolymers and blends thereof.

5. The composition of claim 1 wherein the polyhydroxyalkanoate polymer comprises one or more units which alter the chemical stability of the polymer backbone.

6. The composition of claim 1 wherein the polyhydroxyalkanoate polymer comprises unit(s) promoting chain scission.

7. The composition of claim 6 wherein the units contain more than two functional groups.

8. The composition of claim 1 wherein a heteroatom is incorporated into the polymer backbone chain.

9. The composition of claim 8 wherein the heteroatom is selected from the group consisting of oxygen, sulfur or nitrogen.

10. The composition of claim 6 wherein the units are incorporated into the polymer backbone with chemical linkages selected from the group consisting of ester, amide, ether, carbamate, anhydride, and carbonate.

11. The composition of claim 10 wherein the units are selected from the group consisting of 2-hydroxyacids, 2-hydroxyalkoxyacetic acids, amino acids, amino alcohols, diacids, triols, and tetraols.

12. The composition of claim 11 wherein the 2-hydroxyacids are 2-hydroxyalkanoic acids.

13. The composition of claim 12 wherein the 2-hydroxyalkanoic acid is lactic acid or glycolic acid.

14. The composition of claim 11 wherein the 2-hydroxyacids are 2-hydroxyalkenoic acids.

15. The composition of claim 11 wherein the 2-hydroxyalkoxyacetic acids are selected from the group consisting of 2-hydroxyethoxy acetic acid and 3-hydroxypropoxy acetic acid.

16. The composition of claim 1 wherein the polymer comprises pendant groups that catalyze the degradation of the polymer backbone.

17. The composition of claim 16 wherein the pendant groups are selected from acidic and basic groups.

18. The composition of claim 16 comprising reactant pendant groups that cause polymer chain scission.

19. The composition of claim 18 wherein the reactant pendant groups are selected from nucleophiles and electrophiles.

20. The composition of claim 16 wherein the pendant groups are selected from the group consisting of alcohols, acids, and amine groups.

* * * * *